US006083709A

United States Patent [19]

Reynolds, Jr. et al.

[11] Patent Number: 6,083,709

[45] Date of Patent: Jul. 4, 2000

[54] IMMUNOASSAY FOR DETECTION OF MUTANT P53 POLYPEPTIDE IN SERUM

[75] Inventors: Frederick H. Reynolds, Jr., Syosset, N.Y.; Ron Zeheb, Tucson, Ariz.; John R. Stephenson, Santa Cruz, Calif.; John M. Sorvillo, Sudbury, Mass.

[73] Assignee: OSI Pharmaceuticals, Inc., Uniondale, N.Y.

[21] Appl. No.: 08/094,071

[22] PCT Filed: Jan. 31, 1992

[86] PCT No.: PCT/US92/00878

§ 371 Date: Jul. 28, 1993

§ 102(e) Date: Nov. 23, 1993

Related U.S. Application Data

[63] Continuation-in-part of application No. 07/719,172, Jun. 21, 1991, abandoned, and application No. 07/649,566, Feb. 1, 1991, abandoned, which is a continuation of application No. 07/298,776, Jan. 17, 1989, abandoned, which is a continuation of application No. 06/885,617, Jul. 23, 1986, abandoned, which is a continuation-in-part of application No. 06/767,862, Aug. 21, 1985, abandoned.

[51] Int. Cl.[7] .......... G01N 33/574; G01N 33/53; G01N 33/537; G01N 33/543

[52] U.S. Cl. .......... 435/7.94; 435/7.1; 435/7.5; 435/7.7; 435/7.8; 435/7.9; 435/7.92

[58] Field of Search .......... 435/7.1, 7.2, 7.23, 435/7.5, 7.7, 7.8, 7.9, 7.93, 7.94, 7.95, 960, 968, 7.92

[56] References Cited

U.S. PATENT DOCUMENTS

| | | | |
|---|---|---|---|
| 4,486,530 | 12/1984 | David et al. | 435/7.91 |
| 4,699,877 | 10/1987 | Cline et al. | 424/138.1 |
| 4,786,718 | 11/1988 | Weinberg et al. | 530/387.7 |
| 4,798,787 | 1/1989 | McCormick et al. | 435/7.21 |
| 4,898,932 | 2/1990 | Carney et al. | 530/387.7 |

FOREIGN PATENT DOCUMENTS

| | | |
|---|---|---|
| 0108564 | 5/1984 | European Pat. Off. . |
| 0206065 | 12/1986 | European Pat. Off. . |
| 8500663 | 2/1985 | WIPO . |
| 8500807 | 2/1985 | WIPO . |

OTHER PUBLICATIONS

Banks, L. et al. (1986) Isolation of human–p53–specific monoclonal antibodies and their use in the studies of human p53 expression. J. Biochem. 159:529–534.

Der, C.J. and Cooper, G.M. (1983) Altered gene products are associated with activation of cellular rask genes in human lung and colon carcinomas. Cell 32:201–208.

Der, C.J. et al. (1982) Transforming genes of human bladder and lung carcinoma cell lines are homologous to the ras genes of Harvey and Kirsten sarcoma viruses. PNAS, USA 79:3637–3640.

Gallick, G.E. et al. (1985) Expression of p21$^{ras}$ in fresh primary and metastatic human colorectal tumors. PNAS, USA 82:1795–1799.

Gallo, R.C. and Wong–Staal, F. (1982) Retroviruses as etiologic agents of some animal and human leukemias and lymphomas and as tools for elucidating the molecular mechanism of leukemogenesis, Blood 60(3):545–557.

Hand, P.H. et al. (1984) Monoclonal antibodies of predefined specificity detect activated ras gene expression in human mammary and colon carcinomas. PNAS, USA 81:5227–5231.

Harlow, E. et al. (1981) Monoclonal antibodies Specific for Simian Virus 40 Tumor Antigens. J. of Virology 39(3):861–869.

Kern, S.E. et al. (1991) Identification of p53 as a sequence–specific DNA–binding protein. Science 252:1708–1711.

Milburn, M.V. et al. (1990) Molecular switch for signal transduction: structural differences between active and inactive forms of proto–oncogenic ras proteins. Science 257:939–945.

Pinhasi–Kimhi, O. et al. (1986) Specific interaction between the p53 cellular tumour antigen and major heat shock proteins, Nature 320:182–185.

Sidransky, D. et al. (1991) Identification of p53 Gene Mutations in Bladder Cancers and Urine Samples. Science 252:706–709.

Benchimol et al., EMBO J., 1982, vol. 1, #9:1055–1062.

Mowat et al., Nature, Apr. 18, 1985, 314:633–636.

*Primary Examiner*—Terry A. McKelvey
*Attorney, Agent, or Firm*—John P. White; Cooper & Dunham LLP

[57] ABSTRACT

The invention provides a method for diagnosing in a subject a neoplastic condition which comprises (a) obtaining from the subject a sample of a biological fluid; and (b) detecting the presence in the sample of a mutant p53 polypeptide encoded by an activated p53 oncogene, the presence of the mutant p53 polypeptide in the sample indicating that the subject has the neoplastic condition.

50 Claims, 10 Drawing Sheets p53 ELISA STANDARD CURVE kDa
I II III IV V I
200-
92-
68-
43-
25.7-
18.4-
BSA
p53
p53

MUTANT p53 IN DILUTED MAMMALIAN CELL LYSATES

MUTANT p53 IN MAMMALIAN CELL LYSATES

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
(A) LENGTH: 1757 base pairs
(B) TYPE: nucleic acid
(C) STRANDEDNESS: single
(D) TOPOLOGY: linear (ii) MOLECULE TYPE: cDNA (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Harlow , E.
Williamson, N. M.
Ralston, R.
Helfman, D. M.
Adams, T. E.
(B) TITLE: Molecular Cloning and In-Vitro Expression of a C-DNA Clone for Human Cellular Tumor Antigen P53
(C) JOURNAL: Molecular and Cellular Biology
(D) VOLUME: 5
(E) ISSUE: 7
(F) PAGES: 1601-1610
(G) DATE: July-1985

(xi) SEQUENCE DESCRIPTION: SEQ ID NO:1:

```
GTCGACCCTT TCCACCCCTG GAAGATGGAA ATAAACCTGC GTGTGGGTGG AGTGTTAGGA     60

CAAAAAAAAA AAAAAAAAAG TCTAGAGCCA CCGTCCAGGG AGCAGGTAGC TGCTGGGCTC    120

CGGGGACACT TTGCGTTCGG GCTGGGAGCG TGCTTTCCAC GACGGTGACA CGCTTCCCTG    180

GATTGGCAGC CAGACTGCCT TTCCGGGTCA CTGCCATGGA GGAGCCGCAG TCAGATCCTA    240

GCGTCGAGCC CCCTCTGAGT CAGGAAACAT TTTCAGACCT ATGGAAACTA CTTCCTGAAA    300

AATGCAACGT TCTGTCCCCC TTGCCGTCCC AAGCAATGGA TGATTTGATG CTGTCCCCGG    360

ACGATATTGA ACAATGGTTC ACTGAAGACC CAGGTCCAGA TGAAAAAAAA ATAAAAGCTC    420

CCAGAATGCC AGAGGCTGCT CCCCCCGTGG CCCCTGCACC AGCAGCTCCT ACACCGGCGG    480

CCCCTGCACC AGCCCCCTCC TGGCCCCTGT CATCTTTGGG GTATCTACTG TCCCTTCCCA    540

GAAAACCTAC CAGGGCAGCT ACGGTTTCCG TCTGGGCTTC TTGCATTCTG GGACAGCCAA    600

GTCTGTGACT TGCACGTACT CCCCTGCCAT CTGTAACCTC AACAAGATGT TTTGCCAACT    660

GGCCAAGACC TGCCCTGTGC AGCTGTGGGT TGATTCCACA CCCCCGCCCG GCACCCGCGT    720

CCGCGCCATG GCCATCTCCG ATACAAGCAG TCACAGCACA TGACGGAGGT TGTGAGGCGC    780

TGCCCCCACC ATGAGCGCTG CTCAGATAGC GATGGTCTGG CCCCTCCTCA GCATCTTATC    840
```

-continued

```
CGTGCGAGTG GAAGGAAATT TGCGTGTGGA GTATTTGGAT GACAGAAACA CTTTTCGACA    900

TAGTGTGGTG GTGCCCTATG AGCCGCCTGA GGTTGGCTCT GACTGTTCCG GTTGTACCAC    960

CATCCACTAC AACTACATGT GTAACAGTTC CTGCATGGGC GGCATGAACC GGAGGCCCAT   1020

CCTCACCATC ATCACACTGG AAGACTCCAG TGGTGCACGT GAATCTACTG GGACGGAACA   1080

GCTTTGAGGT GCATGTTTGT GCCTGTCCTG GGAGAGACCG GCGCACAGAG GAAGAGAATC   1140

TCCGCAAGAA AGGGGAGCCT CGTATGTACC ACGAGCTGCC CCCAGGGAGC ACTAAGCGAG   1200

CACTGCCCAA CAACACCAGC TCCTCTCCCC AGCCAAAGAA GAAACCACTG GATGGAGAAT   1260

ATTTCACGAA AGGGCCTTCA GATCCGTGGG CGTGAGCGCT TCGAGATGTT CCGAGAGCTG   1320

AATGAGGCCT TGGAACTCAA GGATGCCCAG GCTGGGAAGG AGCCAGGGGG GAGCAGTTGA   1380

GGGCTCACTC CAGCCACCTG AAGTCCAAAA AGGGTCAGTC TACCTCCCGC CATAAAAAAC   1440

TCATGTTCAA GACAGAAGGG CCTGACTCAG ACTGACATTC TCCACTTCTT GTTCCCCACT   1500

GACAGCCTCC CACCCCCATC TCTCCCTCCC CTGCCATTTT GGGTTTTGGG TCTTTGAACC   1560

CTTGCTTGCA ATAGGTGTGC GTCAGAAGCA CCCAGGACTT CCATTTGCTT TGTCCCGGGG   1620

CTCCACTGAA CAAGTTGGCC TGCACTGGTG TTTTGTTGTG GGGAGGAGGA TGGGGAGTAG   1680

TTTACAATCA GCCACATTCT AGGTAGGGAC CCACTTCACC GTACTAACCA GGGAAGCTGT   1740

CCCTCACTGT TGAATTC                                                  1757
```

(2) INFORMATION FOR SEQ ID NO:2:

(i) SEQUENCE CHARACTERISTICS:
(A) LENGTH: 170 amino acids
(B) TYPE: amino acid
(C) STRANDEDNESS: single
(D) TOPOLOGY: linear (ii) MOLECULE TYPE: protein (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Bartek , J.
Iggo, R.
Lane, D. P.
(B) TITLE: Genetic and immunochemical analysis of mutant p53 in human breast cancer cell lines
(C) JOURNAL: Oncogene
(D) VOLUME: 5
(F) PAGES: 893-899
(G) DATE: 1990

(xi) SEQUENCE DESCRIPTION: SEQ ID NO:2:

```
Gly Thr Ala Lys Ser Val Thr Cys Thr Tyr Ser Pro Ala Leu Asn Lys
1               5                   10                  15

Met Phe Cys Gly Leu Ala Lys Thr Cys Pro Val Gln Leu Trp Val Asp
            20                  25                  30

Ser Thr Pro Pro Pro Gly Thr Arg Val Arg Ala Met Ala Ile Tyr Lys
        35                  40                  45

Gln Ser Gln His Met Thr Glu Val Val Arg Arg Cys Pro His His Glu
    50                  55                  60

Arg Cys Ser Asp Ser Asp Gly Leu Ala Pro Pro Gln His Leu Ile Arg
65                  70                  75                  80

Val Glu Gly Asn Leu Arg Val Glu Tyr Leu Asp Asp Arg Asn Thr Phe
```

```
                85                  90                  95

Arg His Ser Val Val Val Pro Tyr Glu Pro Pro Glu Val Gly Ser Asp
            100                 105                 110

Cys Thr Thr Ile His Tyr Asn Tyr Met Cys Asn Ser Ser Cys Met Gly
        115                 120                 125

Gly Met Asn Arg Arg Pro Ile Leu Thr Ile Ile Thr Leu Glu Asp Ser
    130                 135                 140

Ser Gly Asn Leu Leu Gly Arg Asn Ser Phe Glu Val Arg Val Cys Ala
145                 150                 155                 160

Cys Pro Gly Arg Asp Arg Arg Thr Glu Glu
                165                 170
```

(2) INFORMATION FOR SEQ ID NO:3:

(i) SEQUENCE CHARACTERISTICS:
(A) LENGTH: 169 amino acids
(B) TYPE: amino acid
(C) STRANDEDNESS: single
(D) TOPOLOGY: linear (ii) MOLECULE TYPE: protein (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Bartek , J.
Iggo, R.
Lane, D. P.
(B) TITLE: Genetic and immunochemical analysis of mutant p53 in human breast cancer cell lines
(C) JOURNAL: Oncogene
(D) VOLUME: 5
(F) PAGES: 893-899
(G) DATE: 1990

(xi) SEQUENCE DESCRIPTION: SEQ ID NO:3:

```
Gly Thr Ala Lys Ser Val Thr Cys Thr Tyr Ser Pro Ala Leu Asn Met
1               5                   10                  15

Phe Cys Gly Leu Ala Lys Thr Cys Pro Val Gln Leu Trp Val Asp Ser
            20                  25                  30

Thr Pro Pro Pro Gly Thr Arg Val Arg Ala Met Ala Ile Tyr Lys Gln
        35                  40                  45

Ser Gln His Met Thr Glu Val Val Arg Arg Cys Pro His His Glu Arg
    50                  55                  60

Cys Ser Asp Ser Asp Gly Leu Ala Pro Pro Gln His Phe Ile Arg Val
65                  70                  75                  80

Glu Gly Asn Leu Arg Val Glu Tyr Leu Asp Asp Arg Asn Thr Phe Arg
                85                  90                  95

His Ser Val Val Val Pro Tyr Glu Pro Pro Glu Val Gly Ser Asp Cys
            100                 105                 110

Thr Thr Ile His Tyr Asn Tyr Met Cys Asn Ser Ser Cys Met Gly Gly
        115                 120                 125

Met Asn Arg Arg Pro Ile Leu Thr Ile Ile Thr Leu Glu Asp Ser Ser
    130                 135                 140

Gly Asn Leu Leu Gly Arg Asn Ser Phe Glu Val Arg Val Cys Ala Cys
145                 150                 155                 160

Pro Gly Arg Asp Arg Arg Thr Glu Glu
                165
```

(2) INFORMATION FOR SEQ ID NO:4:

(i) SEQUENCE CHARACTERISTICS:
(A) LENGTH: 169 amino acids
(B) TYPE: amino acid
(C) STRANDEDNESS: single
(D) TOPOLOGY: linear (ii) MOLECULE TYPE: protein (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Bartek , J.
Iggo, R.
Lane, D. P.
(B) TITLE: Genetic and immunochemical analysis of mutant p53 in human breast cancer cell lines
(C) JOURNAL: Oncogene
(D) VOLUME: 5
(F) PAGES: 893-899
(G) DATE: 1990

(xi) SEQUENCE DESCRIPTION: SEQ ID NO:4:

```
Gly Thr Ala Lys Ser Val Thr Cys Thr Tyr Ser Pro Ala Leu Asn Lys
1               5                   10                  15

Met Phe Cys Gly Leu Ala Lys Thr Cys Pro Val Gln Leu Trp Val Asp
            20                  25                  30

Ser Thr Pro Pro Pro Gly Thr Arg Val Arg Ala Met Ala Ile Tyr Lys
        35                  40                  45

Gln Ser Gln His Met Thr Glu Val Val Arg Arg Cys Pro His His Glu
    50                  55                  60

Arg Cys Ser Asp Ser Asp Gly Leu Ala Pro Pro Gln His Ile Arg Val
65                  70                  75                  80

Glu Gly Asn Leu Arg Val Glu Tyr Leu Asp Asp Arg Asn Thr Phe Arg
                85                  90                  95

His Ser Val Val Val Pro Tyr Glu Pro Pro Glu Val Gly Ser Asp Cys
            100                 105                 110

Thr Thr Ile His Tyr Asn Tyr Met Cys Asn Ser Ser Cys Met Gly Gly
        115                 120                 125

Met Asn Arg Ser Pro Ile Leu Thr Ile Ile Thr Leu Glu Asp Ser Ser
    130                 135                 140

Gly Asn Leu Leu Gly Arg Asn Ser Phe Glu Val Arg Val Cys Ala Cys
145                 150                 155                 160

Pro Gly Arg Asp Arg Arg Thr Glu Glu
                165
```

(2) INFORMATION FOR SEQ ID NO:5:

(i) SEQUENCE CHARACTERISTICS:
(A) LENGTH: 170 amino acids
(B) TYPE: amino acid
(C) STRANDEDNESS: single
(D) TOPOLOGY: linear (ii) MOLECULE TYPE: protein (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Bartek , J.
Iggo, R.
Lane, D. P.
(B) TITLE: Genetic and immunochemical analysis of mutant p53 in human breast cancer cell lines
(C) JOURNAL: Oncogene
(D) VOLUME: 5
(F) PAGES: 893-899
(G) DATE: 1990

(xi) SEQUENCE DESCRIPTION: SEQ ID NO:5:

```
Gly Thr Ala Lys Ser Val Thr Cys Thr Tyr Ser Pro Ala Leu Asn Lys
1               5                   10                  15

Met Phe Cys Gly Leu Ala Lys Thr Cys Pro Val Gln Leu Trp Val Asp
            20                  25                  30

Ser Thr Pro Pro Pro Gly Thr Arg Val Arg Ala Met Ala Ile Tyr Lys
        35                  40                  45

Gln Ser Gln His Met Thr Glu Val Val Arg Arg Cys Pro His His Glu
    50                  55                  60

Arg Cys Ser Asp Ser Asp Gly Leu Ala Pro Pro Gln His Leu Ile Arg
65                  70                  75                  80

Val Glu Gly Asn Leu Arg Val Glu Tyr Leu Asp Asp Arg Asn Thr Phe
                85                  90                  95

Arg His Ser Val Val Val Pro Tyr Glu Pro Pro Glu Val Gly Ser Asp
            100                 105                 110

Cys Thr Thr Ile His Tyr Asn Tyr Met Cys Asn Ser Ser Cys Met Gly
        115                 120                 125

Gly Met Asn Arg Arg Pro Ile Leu Thr Ile Ile Thr Leu Glu Asp Ser
    130                 135                 140

Ser Gly Asn Leu Leu Gly Arg Asn Ser Phe Glu Val His Val Cys Ala
145                 150                 155                 160

Cys Pro Gly Arg Asp Arg Arg Thr Glu Glu
                165                 170
```

(2) INFORMATION FOR SEQ ID NO:6:

(i) SEQUENCE CHARACTERISTICS:
(A) LENGTH: 170 amino acids
(B) TYPE: amino acid
(C) STRANDEDNESS: single
(D) TOPOLOGY: linear (ii) MOLECULE TYPE: protein (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Bartek , J.
Iggo, R.
Lane, D. P.
(B) TITLE: Genetic and immunochemical analysis of mutant p53 in human breast cancer cell lines
(C) JOURNAL: Oncogene
(D) VOLUME: 5
(F) PAGES: 893-899
(G) DATE: 1990

(xi) SEQUENCE DESCRIPTION: SEQ ID NO:6:

-continued

```
Gly Thr Ala Lys Ser Val Thr Cys Thr Tyr Ser Pro Ala Leu Asn Lys
1               5                   10                  15

Met Phe Cys Gly Leu Ala Lys Thr Cys Pro Val Gln Leu Trp Val Asp
            20                  25                  30

Ser Thr Pro Pro Pro Gly Thr Arg Val Arg Ala Met Ala Ile Tyr Lys
        35                  40                  45

Gln Ser Gln His Met Thr Glu Val Val Arg Arg Cys Pro His His Glu
    50                  55                  60

Arg Cys Ser Asp Ser Asp Gly Leu Ala Pro Pro Gln His Leu Ile Arg
65                  70                  75                  80

Val Glu Gly Asn Leu Arg Val Glu Tyr Leu Asp Asp Arg Asn Thr Phe
                85                  90                  95

Arg His Ser Val Val Val Pro Tyr Glu Pro Pro Glu Val Gly Ser Asp
            100                 105                 110

Cys Thr Thr Ile His Tyr Asn Tyr Met Cys Asn Ser Ser Cys Met Gly
        115                 120                 125

Gly Met Asn Arg Arg Pro Ile Leu Thr Ile Ile Thr Leu Glu Asp Ser
    130                 135                 140

Ser Gly Asn Leu Leu Gly Arg Asn Ser Phe Glu Val Arg Val Cys Ala
145                 150                 155                 160

Cys Pro Gly Lys Asp Arg Arg Thr Glu Glu
                165                 170
```

(2) INFORMATION FOR SEQ ID NO:7:

(i) SEQUENCE CHARACTERISTICS:
(A) LENGTH: 170 amino acids
(B) TYPE: amino acid
(C) STRANDEDNESS: single
(D) TOPOLOGY: linear (ii) MOLECULE TYPE: protein (iii) HYPOTHETICAL: N (iv) ANTI-SENSE: N (vii) IMMEDIATE SOURCE:
(B) CLONE: activated p53 oncogene (x) PUBLICATION INFORMATION:
(A) AUTHORS: Bartek , J.
Iggo, R.
Lane, D. P.
(B) TITLE: Genetic and immunochemical analysis of mutant p53 in human breast cancer cell lines
(C) JOURNAL: Oncogene
(D) VOLUME: 5
(F) PAGES: 893-899
(G) DATE: 1990

(xi) SEQUENCE DESCRIPTION: SEQ ID NO:7:

```
Gly Thr Ala Lys Ser Val Thr Cys Thr Tyr Ser Pro Ala Leu Asn Lys
1               5                   10                  15

Met Phe Cys Gly Leu Ala Lys Thr Cys Pro Val Gln Leu Trp Val Asp
            20                  25                  30

Ser Thr Pro Pro Pro Gly Thr Arg Val Arg Ala Met Ala Ile Tyr Lys
        35                  40                  45

Gln Ser Gln His Met Thr Glu Val Val Arg Arg Cys Pro His His Glu
    50                  55                  60

Arg Cys Ser Asp Ser Asp Gly Leu Ala Pro Pro Gln His Leu Ile Arg
65                  70                  75                  80

Val Glu Gly Asn Leu Arg Val Glu Tyr Leu Asp Asp Arg Asn Thr Phe
```

-continued

```
                    85                  90                  95

Arg His Ser Val Val Val Pro Tyr Glu Pro Pro Glu Val Gly Ser Asp
            100                 105                 110

Cys Thr Thr Ile His Tyr Asn Tyr Met Cys Asn Ser Ser Cys Met Gly
        115                 120                 125

Gly Met Asn Arg Arg Pro Ile Leu Thr Ile Ile Thr Leu Glu Asp Ser
    130                 135                 140

Ser Gly Asn Leu Leu Gly Arg Asn Ser Phe Glu Val Arg Val Cys Ala
145                 150                 155                 160

Cys Pro Gly Arg Asp Arg Arg Thr Lys Glu
                165                 170
```

IMMUNOASSAY FOR DETECTION OF MUTANT P53 POLYPEPTIDE IN SERUM

This application is a 371 of PCT/US92/00878 filed Jan. 31, 1992, and is a continuation-in-part of U.S. Ser. No. 07/719,172, filed Jun. 21, 1991, now abandoned, and a continuation-in-part of U.S. Ser. No. 07/649,566, filed Feb. 1, 1991, now abandoned, which is a continuation of U.S. Ser. No. 07/298,776, filed Jan. 17, 1989, now abandoned, which is a continuation of U.S. Ser. No. 06/885,617, filed Jul. 23, 1986, now abandoned, which is a continuation-in-part of U.S. Ser. No. 06/767,862, filed Aug. 21, 1985, now abandoned. The contents of all of which are hereby incorporated by reference into the subject application.

BACKGROUND OF THE INVENTION

Throughout this application various publications are referenced by arabic numbers within parentheses. Full citations for these publications may be found at the end of the specification immediately preceding the claims. The disclosures of these publications in their entireties are hereby incorporated by reference into this application in order to more fully describe the state of the art to which this invention pertains.

Cellular oncogenes are normal genes which have been conserved throughout evolution and are believed to have normal functional roles in the cell. In their non-activated (wild-type) state such cellular oncogenes are sometimes referred to as proto-oncogenes. Proto-oncogenes are not oncogenic or tumorigenic until they are activated in some way. A number of different genetic mechanisms may cause the somatic mutation of oncogenes that results in the activated oncogenes found in tumor cells. These include point mutations, translocations, gene rearrangement, and gene amplification, all of which may be induced by chemical or physical carcinogenic means or by the integration of a viral genome adjacent to the proto-oncogene sequences in the host DNA. Certain oncogenes, such as ras and wild type p53 oncogenes, when "activated" encode mutant proteins while others such as myc may express elevated levels of normal protein.

The wild type p53 oncogene encodes wild type p53 polypeptide which functions as a negative regulator of cell division. The wild type p53 polypeptide has been found intracellularly in normal cells and tissues at low levels. Mutant p53 polypeptides encoded by activated p53 oncogenes are present intracellularly at high concentrations in mammalian tumors and tumor cell lines.

The wild type p53 oncogene is conserved across a wide variety of species including man, mouse, rat and frog (1). cDNA sequence analysis has indicated that there are five blocks of very highly conserved sequences (2, 3). These conserved residues have been grouped in blocks beginning at amino acid 117 and ending at amino acid 286 (4). Point mutations, occurring principally in these five blocks of very highly conserved sequences and also in highly conserved regions of the wild type p53 oncogene lying outside of these blocks, produce an activated p53 oncogene (SEQ ID NO:2–SEQ ID NO:7). Changes in these conserved areas have a significant impact on the function of the mutant p53 polypeptide. Changes in these regions of the wild type p53 oncogene generate an activated p53 oncogene which encodes a protein having a conformational change identical to the vast majority of the mutant p53 polypeptides so expressed.

The product of the activated p53 oncogene, i.e. mutant p53 polypeptide, is present at high levels in a high percentage of virtually all classes of human tumors including tumors of the colon, lung, and breast (2). Biochemical analyses of mutant p53 polypeptides demonstrate that activating mutations affect the polypeptide's structure in similar ways. Mutant p53 polypeptides have a much longer half-life as compared to normal p53 polypeptide. In addition, mutant p53 polypeptides are able to complex with the heat-shock-protein-70 family of proteins but not to SV40 large T antigen (5–8). Finally, in histological or cell-based assays, mutant and wild-type p53 polypeptides have been distinguished on the basis of differential reactivity with monoclonal antibodies. Antibody secreted by clone PAb246 is reactive with wild-type p53 polypeptides but not with any mutant p53 polypeptide tested to date, while antibody secreted by clone PAb240 reacts with all mutant p53 polypeptides tested to date but not with a wild-type p53 polypeptide (5–21).

The human, wild-type p53 oncogene is found on chromosome 17p. Allelic loss in 17p occur at high frequency in human breast cancer (22), colon cancer (23), astrocytomas (24) and small cell lung carcinoma (25). The question of allele loss of the wild-type p53 oncogene was addressed by cytogenetic analysis of a number of colon cancer samples using specific DNA probes (23). The results of such analysis indicated that at least a portion, if not all, of one of the two alleles of the wild-type p53 oncogene was lost. However, there were no large deletions or rearrangements in the p53 oncogene associated with the other allele. In most cases, sequence analysis of cDNA from the tumors demonstrated that the p53 oncogene encoded by the second allele contained activating point or missense mutations in those regions encoding the conserved amino acid sequence boxes (26). Mutant p53 polypeptides possess an extended half-life of about 24 hours in comparison to wild-type p53 polypeptides which have a half-life of about 20 minutes. The extended half-life of the mutant p53 polypeptide allows it to accumulate to detectable levels in those tumors associated with an activated p53 oncogene. In contrast, wild type p53 polypeptide does not accumulate and is not easily detected. Because the wild-type p53 polypeptide is barely detectable in normal cells, due to its extremely short half-life, the presence of substantial amounts of p53 polypeptide establishes that the protein contains both a mutation resulting in extended half-life and the consequent phenotype of a dominant oncogenic protein. Stabilization of the mutant p53 polypeptide may be due to its ability to form complexes with other molecules such as heat shock proteins. Alternatively, stabilization of the mutant p53 polypeptide may be due to mutations in the primary sequence of the polypeptides which make them intrinsically more stable. Further alternatively, stabilization of the mutant p53 polypeptide may be due to post-translational modifications such as hyperphosphorylation (5–8, 27).

As previously discussed, the wild-type p53 oncogene is mutated at high frequency in the majority of human cancers. One of the first indications that p53 polypeptide expression may have been associated with some forms of human cancer was the observation that about 9% of patients with breast carcinoma (14 out of 155 samples tested) had auto-antibodies to p53 polypeptides (28). The occurrence of autologous antibodies directed against p53 polypeptides in patients with tumors indicated that the p53 polypeptide associated with the tumor was sufficiently altered so that it became immunogenic. It is important to note that at the time of such findings it was not possible to distinguish whether the auto-antibodies so observed were directed against wild-type or mutant p53 polypeptides (28). Indeed, the very existence of mutant p53 polypeptides had not been recognized at the time such auto-antibodies to p53 polypeptides were observed (28).

One early study found that tumors from 24% of breast cancer patients showed elevated levels of p53 polypeptide (17). An additional study showed that 40% of human breast cancer biopsies showed elevated levels of p53 polypeptides (18). Similarly, up to 55% of colon cancer tumor samples showed overexpression of p53 polypeptide based upon immunohistochemical data (19). None of these assays distinguished between wild-type and mutant p53 polypeptides.

In 1990, a more extensive study using the monoclonal antibody PAb240, which is selectively reactive with mutant p53 polypeptides, was performed. This study found that mutant p53 polypeptides could be detected in 50% of colon cancer, 30% of breast cancer and 70% of lung cancer tumor sections (4). However, mutant p53 polypeptides could not be detected in any normal or premalignant tissues from these patients. Other investigations have found overexpression of mutant p53 polypeptide in patients with leukemia or lymphoma (20, 21, 29). It is becoming increasingly apparent that when proper care is taken to preserve the specimen, a high percent of cancer biopsies examined are found to express elevated amounts of mutant p53 polypeptide.

Before applicants invention, histopathology had been the only technique which showed the correlation between mutant p53 polypeptides and neoplasia. The literature described monoclonal antibodies which specifically recognize and bind mutant p53 polypeptides, however, such antibodies did not (1) detect mutant p53 polypeptides in biological fluids or (2) imply that detection of mutant p53 polypeptide in biological fluids could effect the diagnosis of or monitor neoplastic conditions. Moreover, since mutant p53 polypeptides are located in the interior of the cell, one of ordinary skill in the art would not expect to detect mutant p53 polypeptides in substantially cell-free biological fluids. Thus, this invention is based upon the discovery that normally intracellular, mutant p53 polypeptides may be detected in biological fluids such as serum and that such detection may be utilized to diagnose or monitor neoplastic conditions or states. Accordingly, the establishment of a serum-based diagnostic marker for human cancer would have significant commercial applications. Using assay kits, blood drawn from patients could be routinely and easily assayed for mutant p53 polypeptide concentration. The correlation between the measured mutant p53 polypeptide concentration and the presence of neoplastic disease in the subject patient provides a means for early detection of the cancer. In addition, because of the ease for effecting the invention described herein a much larger segment of the population can be tested. Furthermore, the invention should have wide applicability in basic- and clinical- research applications.

SUMMARY OF THE INVENTION

The present invention provides a method for diagnosing in a subject a neoplastic condition. This method comprises (a) obtaining from the subject a sample of a biological fluid and (b) detecting the presence in the sample of a mutant p53 polypeptide encoded by an activated p53 oncogene, the presence of the mutant p53 polypeptide in the sample indicating that the subject has the neoplastic condition. The present invention also provides a method for diagnosing in a subject a neoplastic condition which comprises (a) obtaining from the subject a sample of a biological fluid; and (b) quantitatively determining the concentration in the sample of a mutant p53 polypeptide encoded by an activated p53 oncogene the presence of the mutant p53 polypeptide in the sample indicating that the subject has the neoplastic condition.

DETAILED DESCRIPTION OF THE INVENTION

Figure 1:
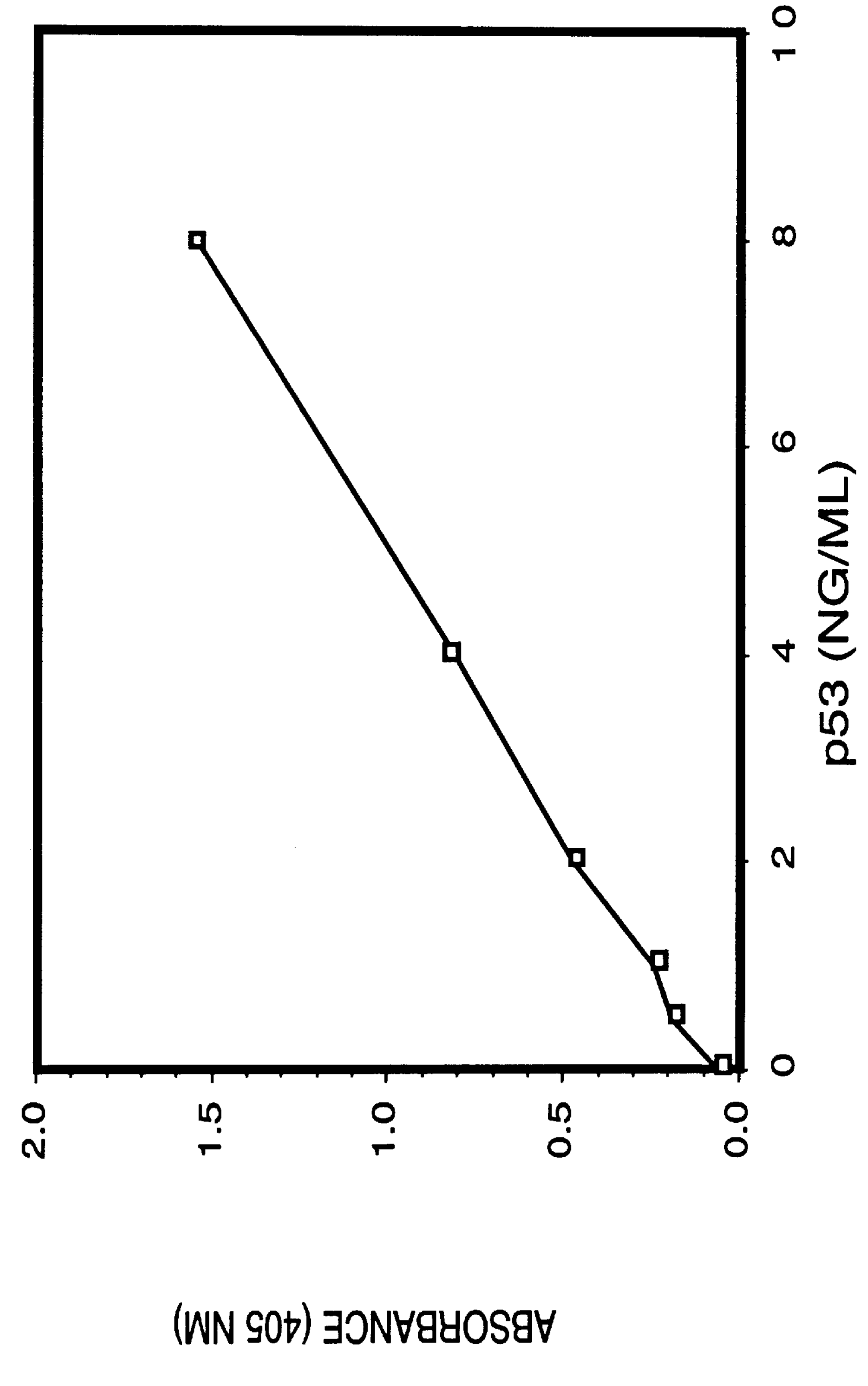
FIG. 1 A standard curve constructed using purified human recombinant mutant p53 polypeptide. The assay detects the purified standard with a sensitivity of approximately 30 pg/ml.

The present invention provides a method for diagnosing in a subject, for example, a human, a neoplastic condition which comprises (a) obtaining from the subject a sample of a biological fluid and (b) detecting the presence in the sample of a mutant p53 polypeptide encoded by an activated p53 oncogene. In this method the presence of the mutant p53 polypeptide in the sample indicates that the subject has the neoplastic condition.

As used in this application a "neoplastic condition" means a state characterized by tumor formation and tumor growth. Examples of neoplastic conditions which may be diagnosed in accordance with this invention include the following forms of human cancer: breast cancer, colon cancer, lung cancer, lymphoma, hepatoma and leukemia, astrocytomas, and small cell lung carcinomas.

Additionally, as used herein, a biological fluid is any body fluid or any fluid derived from a biological sample. Examples of body fluids include urine, blood, sputum, amniotic fluid, saliva, any mucous-type bodily secretion or cerebrospinal fluid. Examples of fluids derived from biological samples include serum, plasma, cell extracts, lung lavage or ascites fluid. Serum is preferred.

Cell extracts may be derived from tumor cells or tissues, normal tissues, or cell lines continuously growing in culture. It would be clear to those skilled in the art that such cells may be from any mammal such as rats, moles, shrews, monkeys, bats, hares, rabbits, dogs, cats, whales, dolphins, elephants, horses, cows, deer, and man.

As used in this application "detecting the presence" means detection by any manner. Further, as used herein "mutant p53 polypeptide" means any polypeptide encoded by an activated p53 oncogene. As used herein "oncogene" means a gene that has the potential to cause cancer. Additionally, the term "activated," in the case of a p53 oncogene, is a condition which induces the onset of cancer, neoplasia, or more generally oncogenesis. Specifically, the condition is caused by a mutation such as a point mutation in a p53 oncogene.

In one example of this invention, the detecting in step (b) comprises: (i) contacting the sample from step (a) with a protein capable of forming a complex with the mutant p53 polypeptide under conditions permitting the complex to be formed; and (ii) determining whether any complex is so formed, the presence of the complex indicating that the subject has the neoplastic condition.

In accordance with the practice of the invention, the protein of step (i) may be an antibody. In one example of the invention the antibody is a polyclonal antibody. In another example the antibody is a monoclonal antibody.

As used herein the term "antibody" means any immunologically reactive molecule (i.e. protein, polypeptide, or fragment thereof) that is naturally occurring or produced by genetic engineering methods or otherwise. Moreover, the antibody may possess an isotype selected from a group comprising an IgG, IgA, IgD, IgE, or IgM isotype or any combination thereof. The antibody may be constructed by fusion of fragments of selected isotypes, expressed in a recombinant system, or generated through hybridoma technology.

In another example of the above-described method, the protein is a heat shock protein. The heat shock protein may be selected from the group consisting of HSC 70–72 and HSP 70–72.

In one example of the above-described invention, the protein specifically forms a complex with the mutant p53 polypeptide. As used herein the word "specifically forms a complex" means that the aforementioned protein only recognizes and binds to a mutant p53 polypeptide. One example of the protein is an antibody, e.g. the PAb240 monoclonal antibody.

Further, the protein may be attached to a solid support. Examples of a solid support include a nylon membrane, a nitrocellulose membrane, a cellulose acetate membrane, an epoxy-activated synthetic copolymer membrane, agarose, Sepharose, a plastic or glass tube or any part thereof, a plastic or glass plate or bead or any part thereof.

In another example of the aforementioned method, in step (ii), the determination whether any complex is formed comprises: a) contacting the sample from step (i) with a second protein capable of forming a second complex with any complex formed in step (i) under conditions permitting the second complex to be formed; and b) determining the presence of any such second complex so formed, the presence of any such second complex indicating that the subject has the neoplastic condition.

In the aforementioned method, the second protein may be a heat shock protein. The heat shock protein may be selected from the group consisting of HSC 70–72 and HSP 70–72.

Optionally, the second protein may be an antibody such as a polyclonal antibody or monoclonal antibody. In one example, the second protein specifically forms a complex with the mutant p53 polypeptide.

Optionally, the protein may be attached to a solid support. Further, the protein may be labeled with a detectable marker.

Also, the second protein may be labeled with a detectable marker. Examples of detectable markers include enzymes, biotins, fluorophores, chromophores, heavy metals, paramagnetic isotopes, or radioisotopes.

The present invention also provides a method for diagnosing in a subject a neoplastic condition which comprises (a) obtaining from the subject a sample of a biological fluid; and (b) quantitatively determining the concentration in the sample of a mutant p53 polypeptide encoded by an activated p53 oncogene, an elevated concentration of the mutant p53 polypeptide in the sample indicating that the subject has the neoplastic condition. Preferably, an elevated concentration is one which is equal to or greater than two standard deviations above the concentration found in samples from normal subjects.

In one example of the above-described method, in step (b), the quantitatively determining comprises: (i) contacting the sample from step (a) with a protein capable of forming a complex with the mutant p53 polypeptide under conditions permitting the complex to be formed; and (ii) determining the quantity of any complex so formed, the presence of the complex indicating that the subject has the neoplastic condition.

In an example of the above-described method, the protein is a heat shock protein. The heat shock protein may be selected from the group consisting of HSC 70–72 and HSP 70–72.

In accordance with the practice of this method, the protein may be an antibody such as a polyclonal antibody or a monoclonal antibody. Further, the protein may be attached to a solid support. Additionally, the protein may specifically form a complex with the mutant p53 polypeptides. An example of such a protein is the PAb 240 monoclonal antibody.

Further, in one embodiment of the above-described method, the quantitative determination whether any complex is formed in step (ii) comprises: a) contacting the sample from step (i) with a second protein capable of forming a second complex with any complex formed in step (i) under conditions permitting the second complex to be formed; and b) determining the quantity of any such second complex so formed and comparing the amount so determined to the amount in a sample from a normal subject the presence of a significantly different amount indicating that the subject has the neoplastic condition.

In an example of the above-described method, the second protein is a heat shock protein. The heat shock protein may be selected from the group consisting of HSC 70–72 and HSP 70–72.

In accordance with the practice of this method, the second protein may be an antibody, e.g. a polyclonal or monoclonal antibody. Optionally, the protein may specifically form a complex with the mutant p53 polypeptide.

Further, the second protein may be attached to a solid support. In accordance with the practice of this method, the second protein may be labeled with a detectable marker.

The detectable marker may be an enzyme, biotin, a fluorophore, a chromophore, a heavy metal, a paramagnetic isotope, or a radioisotope.

This invention further provides a method for quantitatively determining the concentration of p53 in a biological fluid sample which comprises (a) contacting a solid support with an excess of a first antibody under conditions permitting the antibody to attach to the surface of the solid support; (b) contacting the resulting solid support to which the first antibody is bound with a biological fluid sample under conditions such that any p53 polypeptide in the biological fluid binds to the antibody and forms a complex therewith; (c) contacting the complex formed in step (b) with a predetermined amount of a second antibody directed to an epitope on p53 different from the epitope to which the first antibody of step (a) is directed, so as to form a complex which includes p53, the first antibody, and the second antibody; (d) quantitatively determining the amount of the complex formed in step (c); and (e) thereby determining the concentration of p53 in the biological fluid sample.

Also, in one example of this method, the first antibody bound to the solid support is a monoclonal antibody and the second antibody is a polyclonal antibody. Additionally, in another example of the invention, the first antibody bound to the solid support is a polyclonal antibody and the second antibody is a monoclonal antibody. Optionally, the first antibody bound to the solid support is a polyclonal antibody and the second antibody is a polyclonal antibody. Alternatively, the first antibody bound to the solid support is a monoclonal antibody and the second antibody is a monoclonal antibody.

In accordance with the practice of this method, the first antibody may be labeled with a detectable marker. Optionally, the second antibody may be labeled, separately or in addition to the first antibody, with a detectable marker. Examples of suitable detectable markers includes an enzyme, biotin, a fluorophore, a chromophore, a heavy metal, a paramagnetic isotope, or a radioisotope.

This invention provides a method for monitoring the course of a neoplastic condition in a subject which comprises quantitatively determining in a first sample of a biological fluid from the subject the presence of a mutant p53 polypeptide according to any of the previously-described methods and comparing the amount so determined with the amount present in subsequent samples from the subject, such samples being taken at different points in time, i.e. one sample taken at a sufficient period after the other sample to allow for tumor growth or regression. A difference in the amounts determined being indicative of the course of the neoplastic condition, e.g. growth or regression. In the context of this invention, a neoplastic condition includes, but is not limited to carcinomas of the lung, bladder, breast, uterus, prostate, colon, adenocarcinoma of the lung, neuroblastomas, melanomas, rhabdomyosarcomas, lymphomas or leukemias.

Finally, the present invention also provides a kit useful for the detection of a mutant p53 comprising: a) obtaining from the subject a sample of a biological fluid; and b) detecting the presence in the sample of a mutant p53 polypeptide encoded by an activated p53 oncogene, the presence of the mutant p53 polypeptide in the sample indicating that the subject has the neoplastic condition.

Pursuant to the provisions of the Budapest Treaty on the International Recognition of Deposit of Microorganisms For Purpose of Patent Procedure, the hybridomas listed below have been deposited with the American Type Culture Collection ("ATCC"), 10801 University Boulevard, Manassas, Va. 20110-2209, U.S.A.:

1. a hybridoma designated PAb 1801, deposited on Jan. 15, 1991 under ATCC Accession No. HB 10642;
2. a hybridoma designated PAb 421, deposited on Jan. 15, 1991 under ATCC Accession No. HB 10643;
3. a hybridoma designated PAb 240, deposited on Nov. 28, 1990 under ATCC Accession No. HB 10614.

This invention is illustrated in the Experimental Detail section which follows. This section is set forth to aid in an understanding of the invention but is not intended to, and should not be construed to, limit in any way the invention as set forth in the claims which follow thereafter.

Experimental Details

Materials and Methods

Sample Handling Protocols: Serum or plasma samples collected using heparin, EDTA or oxalate may be stored frozen at −70° C. prior to analysis, or alternatively, the samples may be assayed immediately. Serum and/or plasma samples may be analyzed neat (i.e. undiluted) or alternatively the samples may be diluted with Sample Diluent (PBS, pH 7.4 containing 50 mM NaCl, 0.1% BSA, 0.5% Tween-20, 0.02% Thimerosal and 1% (v/v) normal mouse serum). The dilution ratio is dependent on the mutant p53 polypeptide content of the sample and must be determined empirically. Samples are analyzed in duplicate, 100 μl per well. In some instances, autologous antibodies to mutant p53 polypeptide may be present in patient serum and/or plasma samples. The presence of these antibodies may, in some instances, interfere with and/or reduce the sensitivity with which the mutant p53 polypeptide is detected in those samples. Under these conditions, the following additional procedures should be employed. To 500 microliter of sample add an equal volume of acidification buffer (200 mM glycine-HCl, pH 2.0) and incubate for 5 min on ice (4° C.). Add one tenth volume (i.e. 100 microliter added to a 1 ml sample) of neutralization buffer (2M Tris-HCl, pH 8) to the acidified sample and immediately proceed with the assay.

The acidified and neutralized sample may be analyzed directly or after further dilution with Sample Diluent. Alternatively, the acidified sample may be applied to a column of Sephadex G-100 superfine (Pharmacia, Cat No. 17-0061-01). The column effluent is monitored using a spectrophotometer adjusted to 280 nm. The first peak of 280 nm-absorbing material (containing proteins of molecular mass greater than 100 kDa, including any autologous antibodies) is discarded. The remaining peaks, eluting after the first, are pooled and analyzed for mutant p53 polypeptide. The eluted, pooled sample may be stored frozen at −20° C. and/or concentrated by lyophilization prior to analysis for mutant p53 polypeptide.

Urine: Freshly collected urine is pH buffered by the addition of 1/10 volume of urine buffer (1M Tris-HCl, pH 8.0, containing 0.2% Thimerosal). Buffered samples may be stored frozen or analyzed immediately as described above.

Cell extracts: To measure the concentration of mutant p53 in cells, a fluid extract must first be prepared. Numerous extraction protocols can be used. The following protocol provided is an example of a whole cell extraction procedure and should not be constructed as necessarily being the method of choice. Pellet cells by centrifugation (1000×g, for 10 min at 4° C.) then wash 3 times with 20 to 30 cell pellet volumes of ice-cold PBS. Pellet cells and discard PBS wash. Add 5 cell pellet volumes of ice-cold swelling buffer (20 mM Tris/HCl, 5 mM EDTA, 1 mM PMSF, pH 8) and incubate on ice for 30 minutes. Gently resuspend cells every 10 minutes. Add non-ionic detergent (e.g. Tween-20) to a final concentration of 1% (v/v) and continue to incubate on ice for an additional 30 minutes, Resuspend cells every 10 minutes. Add NaCl to a final concentration of 0.5M. Incubate for 15 minutes on ice. Resuspend every 5 minutes. Pellet at approximately 70,000×g for 30 minutes at 4° C. (e.g. 70.1 Ti at 30,000 RPM). Carefully collect the membrane-free supernatant. Supernatant (whole cell extract) may be analyzed for mutant p53 concentration immediately, or stored frozen at −70° C. for later analysis.

Antibody and reagent preparation. Antibodies may be bound to a solid support and used to capture mutant p53 polypeptide. Affinity purified anti-mutant p53 polypeptide polyclonal antibodies may be used as the reporter reagent.

Monoclonal antibody coated plates. Purified monoclonal antibody from clone PAb421 or alternatively from clone PAb1801 or from clone PAb240 is diluted to 5 μg/ml in 100 mM sodium carbonate buffer, pH 9. 100 μl of the diluted antibody solution is added to each well of a 96-well plate (Immulon 1). The plate is then covered with plastic wrap and allowed to incubate for 16 hours at 4° C., or alternatively, for 3 h at 37° C. Wells are emptied and washed once with 200 μl Wash Buffer (PBS containing 0.05% Tween-20 and 0.02% Thimerosal). After washing, the wells are emptied and blocked for 4 h at room temperature with 200 μl of blocking buffer (PBS containing 1% BSA, pH 7.4). After blocking, the wells are emptied and washed 3 times using 200 μl Wash Buffer per well per wash. Coated and blocked wells are stored at 4° C. with 200 μl of PBS containing 0.02% Thimerosal per well. Alternatively, the wells are lyophilized for 4 to 16 h at 4° C. then stored in vacuo in sealed bags.

PAb421 is an $IgG_{2a}$ which binds mammalian wild-type and mutant p53 polypeptides near the carboxyl terminal domain (30). PAb1801 is an $IgG_1$ which binds in the amino terminal domain of human wild-type and mutant p53 polypeptide. PAb240 is an $IgG_1$ isotope which binds only the mutant form of native (i.e. undenatured) human p53 polypeptide. However, this clone will bind mammalian wild-type p53 polypeptide if the protein has been denatured (as in a Western blot). This antibody recognizes a conformationally sensitive epitope near the middle of the mutant p53 polypeptide (residues 156–214 of denatured mouse mutant p53 polypeptide).

Polyclonal antibody coated plates. In an optional procedure, affinity purified polyclonal anti-mutant or wild-type p53 polypeptide antibodies may be coated onto plates according to a method which is identical in every respect with the one described above for monoclonal antibody coated plates.

Purified human recombinant mutant p53 polypeptide. A mutant p53 polypeptide standard curve (see FIG. 1) is constructed using recombinant human p53 polypeptide mutated to contain a histidine residue at position 273 (Hup53 HIS273) (30). For the practice of this invention, any of a series of mutations occurring in highly conserved sequences of the human p53 oncogene, and resulting in the formation of a mutant protein having the characteristics previously disclosed would be functionally equivalent. The cloning and expressing of mutant p53 polypeptide follows established techniques in molecular biology. A cDNA library is constructed (e.g. in pUC8 or pUC9 plasmids) using mRNA extracted from A431 cells (express Hup53 HIS273) as described by Harlow et. al. (30) (SEQ ID NO:1). The cDNA library, so constructed, is screened for the presence of p53 oncogene sequences by hybridization with a complementary cDNA probe as described (30). Colonies which carry activated p53 oncogene sequences are isolated, and the plasmids purified as described (31) and sequenced (30, 32). Sequence encoding the mutant p53 polypeptide is then subcloned into a plasmid expression vector such as pUR291 (33). This construct, encoding a β-galactosidase-mutant p53 polypeptide fusion protein, is grown in *E. coli* (strain LE392) cultures for 16–18 h at 37° C. in the presence of 100 μl/ml isopropyl β-thiogalactoside. Cells are collected, washed with PBS and lysed (31). The mutant p53 polypeptide fusion protein is purified from the cell lysate by immunoaffinity chromatography using a PAb421-agarose column.

Alternatively, a PAb240-agarose column can be used to purify the mutant p53 polypeptide fusion protein. The purified recombinant protein is diluted to an intermediate concentration of 8 μg/ml in PBS containing 0.1% BSA. This is further diluted into sample diluent (PBS containing 50 mM NaCl, 0.5% Tween-20, 0.1% BSA and 0.02% Thimerosal, pH 7.4) to make solutions containing mutant p53 polypeptide at concentrations of 0, 0.125, 0.500, 1.0, 2.0, 4.0 and 8.0 ng/ml, or any other concentration appropriate to the dynamic range of the assay.

Figure 2:
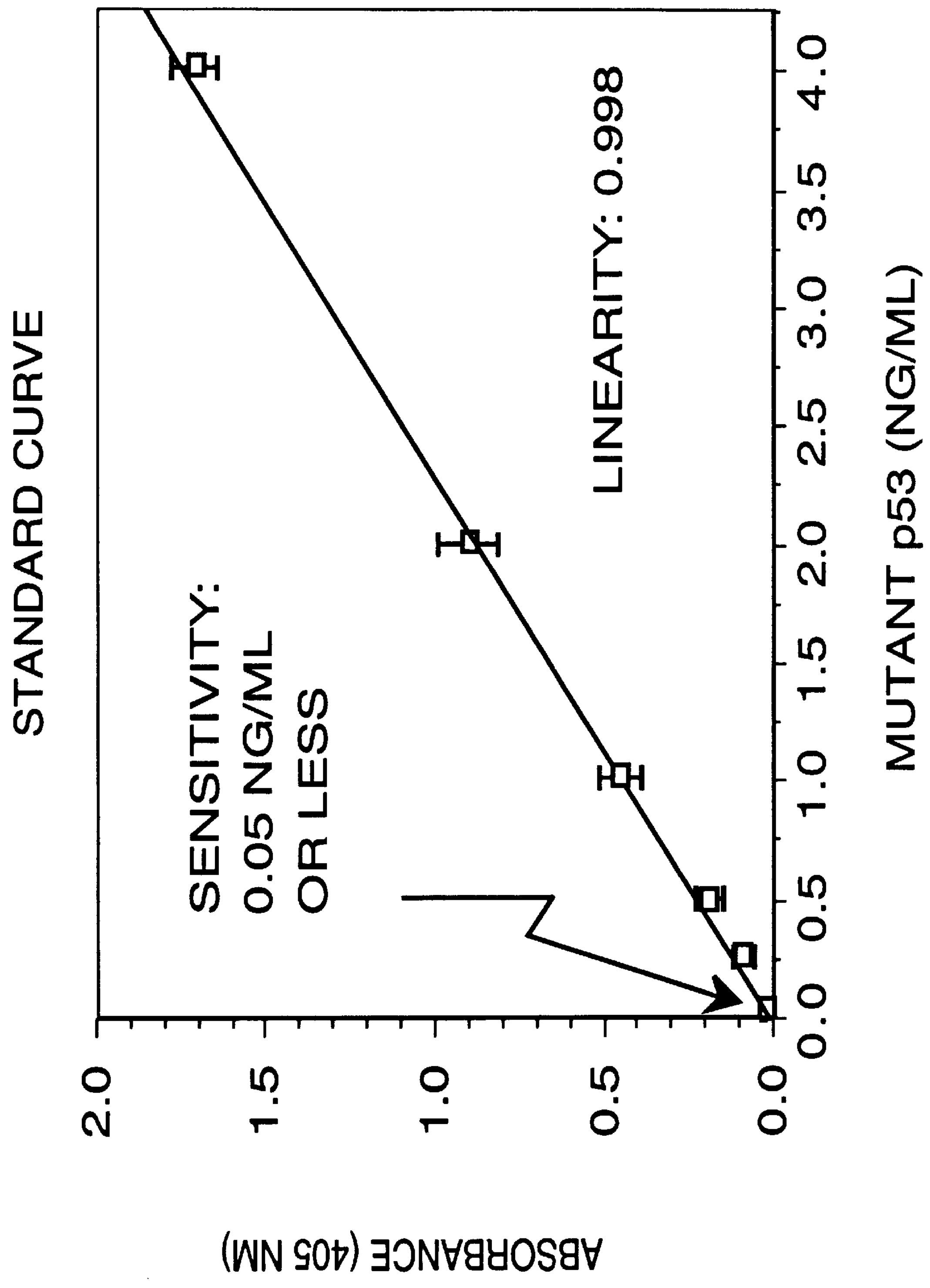
FIG. 2 Line graph showing a standard curve constructed using purified recombinant mutant p53 polypeptide (Hup53HIS273) which was expressed using the T7 expression system.
Figure 3A:
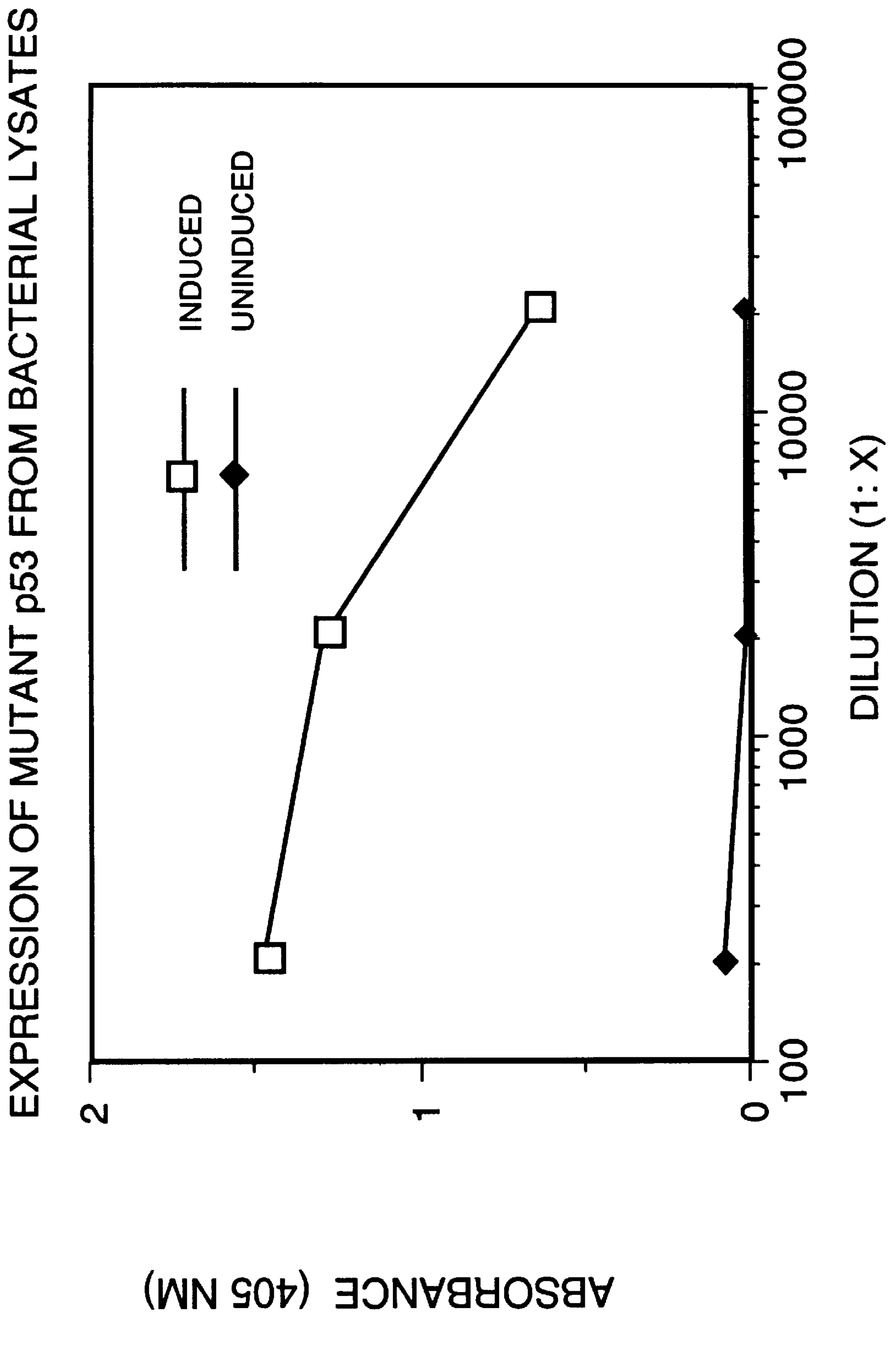
FIG. 3A A line graph of mutant p53 from bacterial lysates. 2 $\mu$l of lysed bacterial pellets were resolved on 10% acrylamide gels, electroblotted onto nitrocellulose and incubated with polyclonal rabbit anti-mutant p53 antibodies.
Figure 3B:
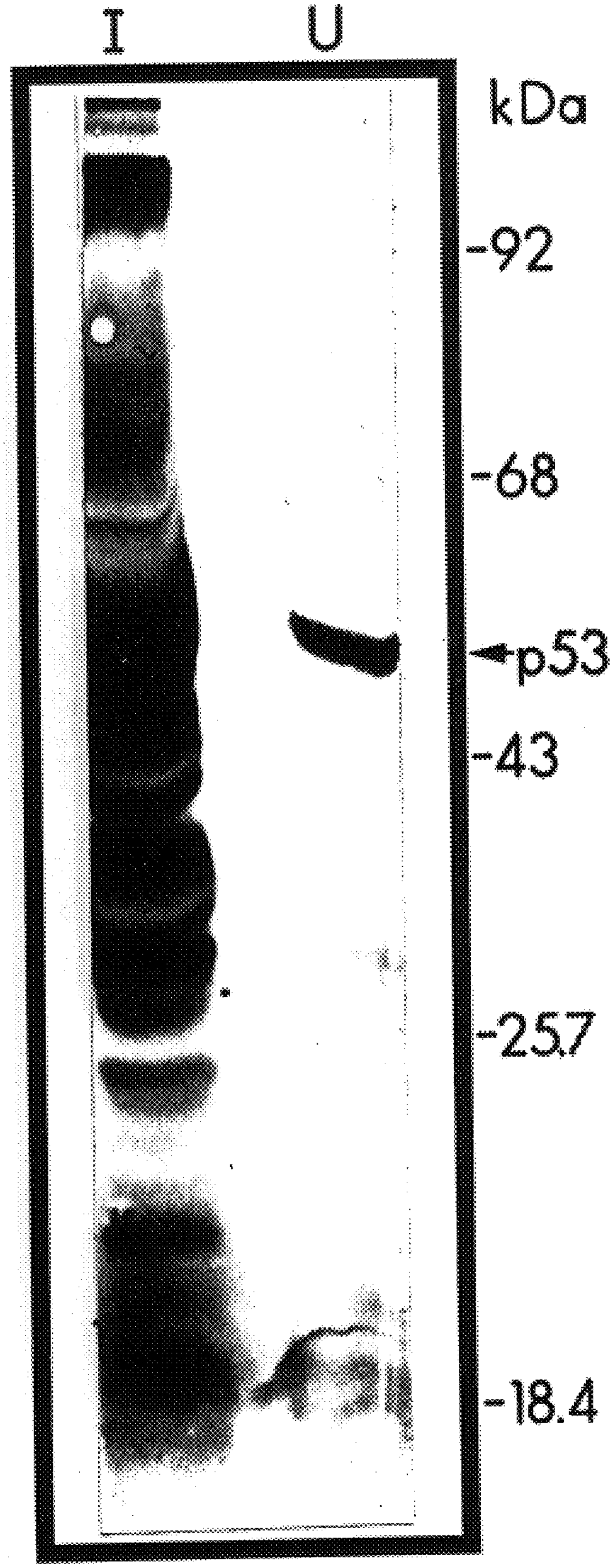
FIG. 3B A photograph of a gel. *E. Coli* strain BL21 (DE3) lysS transfected with mutant human p53 cDNA in the T7 expression plasmid pT7-7 was incubated for 3 h in the presence (I) or absence (U) of 0.4 mM isopropyl-1-thio-β-D-galactoside (IPTG). Washed bacteria were lysed, diluted with Sample Diluent and analyzed for mutant p53 in the ELISA assay.

Subsequently, a second standard curve (FIG. 2) was constructed using recombinant human p53 polypeptide (Hup53 HIS273) expressed using another bacterial expression system. Specifically, *E. coli* strain BL21 (DE3)LysS was transfected with mutant human p53 cDNA cloned into the T7 expression plasmid pT7-7. The transfected bacteria were incubated for 3 hours in the presence of 0.4 mM IPTG. Washed bacteria were lysed and purified as described above, diluted with sample diluent and used to construct a standard curve for mutant p53 in the ELISA assay (FIG. 3 and Table 1).

TABLE 1

Inter- and Intra-assay precision determined at 3 points along the standard curve shown above.

I. Inter-assay Precision
Samples containing three different concentrations of mutant p53, diluted in sample diluent, were analyzed in 8 separate assays.

| Sample | 1 | 2 | 3 |
|---|---|---|---|
| n | 8 | 8 | 8 |
| mean (ng/ml,) | 4.012 | 0.991 | 0.274 |
| standard deviation | 0.120 | 0.042 | 0.065 |
| % CV | 3.0 | 4.2 | 23.7 |

II. Intra-assay Precision.
Samples containing three different concentrations of mutant p53, diluted in sample diluent, were analyzed 8 times each during the course of a single assay.

| Sample | 1 | 2 | 3 |
|---|---|---|---|
| n | 8 | 8 | 8 |
| mean (ng/ml) | 4.044 | 1.043 | 0.260 |
| standard deviation | 0.185 | 0.052 | 0.026 |
| % CV | 4.6 | 5.0 | 10.0 |

Rabbit polyclonal antibodies directed against mutant p53 polypeptide. Female New Zealand White rabbits are immunized with purified recombinant mutant p53 polypeptide following a standard protocol. Specifically, the mutant p53 polypeptide (0.1 mg) is emulsified with RIBI™ adjuvant and administered perilymph nodally. Three weeks later, the rabbits are given an intramuscular boost (0.05 mg antigen/animal). Boosts are continued at 21 day intervals. Serum is collected and the antibody titer determined by ELISA 10 days following each boost. Once a high titer is achieved, serum is collected and the antibody purified as described below.

Antisera, collected as described above, is titered by ELISA. Purified recombinant mutant p53 polypeptide is absorbed onto microtiter wells (1 μg/ml in 0.1M sodium carbonate buffer, pH 9.0; 50 μl/well) for 16 to 20 h at 4° C. The antigen solution is discarded and unoccupied protein binding sites blocked using 200 μl of PBS containing 1% BSA (pH 7.3, for 2 h at room temperature). Duplicate wells are incubated for 3 hours at 37° C. with antisera diluted in buffer (serial 5-fold dilutions starting at 1:500 and ending at 1:312,500; plus a no antiserum control). Bound antibody is detected by incubation with peroxidase-conjugated goat anti-rabbit antibody (2–3 h at 37° C.), followed by addition of a peroxidase substrate. Absorbance is measured using a dual beam, 96-well microtiter plate reader (Bio-Tek Instruments, Model EL320). Antiserum titer is defined as the dilution yielding an absorbance which is twice background absorbance.

Antibodies from rabbits yielding a high serum titer is purified as described below, and further evaluated for suitability as a reporter reagent in a two-site sandwich ELISA assay for mutant p53 polypeptide.

Antibody purification. Antibody (Ig) reactive with human, mutant p53 polypeptide is purified from hyperimmune rabbit sera by immunoaffinity chromatography. Purified, recombinant mutant p53 polypeptide is coupled to CNBr-activated Sepharose 4B (Pharmacia). Crude antisera is clarified by centrifugation at 10,000×g for 30 min., and crude antibody obtained by precipitation with ammonium sulfate. The Ig-enriched preparation is applied to the mutant p53 polypeptide-Sepharose, and the bound antibody eluted using 100 mM glycine-HCl, pH 2.5 and neutralized with 2.0M Tris-HCl, pH 8.0. In a second example, IgG reactive with human mutant p53 polypeptide is purified from hyperimmune rabbit sera by affinity chromatography using Protein A-Sepharose according to a protocol identical to that described above.

Polyclonal antibody recognizes multiple epitopes common to both mutant and wild-type p53 polypeptides. In one instance, polyclonal antibody directed against a p53 polypeptide is paired with a monoclonal capture antibody which binds both wild-type and mutant p53 polypeptide (i.e. clone PAb421). In a second instance, polyclonal antibody directed against a p53 polypeptide is paired with a monoclonal capture antibody which specifically recognizes and binds to mutant p53 polypeptide (i.e. clone PAb240). In a further instance, the polyclonal antibody could be made specific for mutant human p53 polypeptides by adsorption against purified wild-type human p53 polypeptide which has been bound to a solid support, such CNBr-Sepharose or polystyrene tubes.

Native, wild-type p53 polypeptide may be used for the adsorption of rabbit polyclonal antibodies to yield a mutant p53 polypeptide-specific reagent and as a negative control for the assay.

Mouse monoclonal antibodies directed against p53 polypeptide. p53-β-galactosidase fusion proteins (see above) are purified by SDS-polyacrylamide gel electrophoresis. The band corresponding to the fusion protein is excised from the gel and washed in a solution of 1% SDS, 0.2M Tris/acetate pH 8.0, 0.1% DTT. The protein is then electroeluted, dialyzed against 20 mM ammonium bicarbonate, 0.02% SDS and injected into BALB/c mice. Mice are immunized intraperitoneally with 5 μg on days 0, 7, and 14. On day 28 the sera are tested against mutant p53 polypeptide-β-galactosidase fusion protein by ELISA. Mice are boosted with 5 μg of the same antigen and spleen cells are fused to NS1 myeloma fusion partner using established procedures (37). Hybridomas are screened by ELISA against mutant p53 polypeptide-β-galactosidase fusion protein. Additionally, clones reacting with mutant p53 polypeptide fusion protein but not with pure β-galactosidase are subcloned twice by limiting dilution. Hybridomas are grown as ascites-tumors in mice and antibody is purified as previously described (39).

Covalent Coupling of Monoclonal Antibodies to Affi-Gel-10™. Purified monoclonal antibodies to mutant p53 polypeptide are dialyzed against PBS at 4° C. and the Affi-Gel-10 (Bio-Rad) is added to the purified monoclonal antibody solution at a concentration of 7.0 mg of protein per ml of Affi-Gel-10. Generally 70 mg of antibody ligand is added to 10 ml of Affi-Gel-10. The solution is gently agitated on a Labquake rotator (Labindustries #400-10) for four hours at 4° C. followed by the addition of ethanolamine (Eastman Kodak) at a final concentration of 0.1M to block unreacted ester groups. After one hour, the gel matrix is washed extensively with PBS by centrifugation at 2,500 RPM for 10 minutes until the gel is free of reactants as judged by obtaining zero absorbance at 280 nm ($OD_{280}$). To ensure that antibody function is maintained following the coupling procedure, the capture gel matrix is incubated with sera containing mutant p53 polypeptide and bound protein eluted with sample buffer for analysis by SDS-PAGE.

Biotinylation of Purified Antibody For Use in the Antigen Capture Procedure. Monoclonal or polyclonal antibodies are biotinylated according to a protocol distributed by LKB Laboratories. Two hundred microliters of Act BIOTIN solution prepared by adding 2.0 mg of Act BIOTIN to 0.5 ml of anhydrous dimethylformamide (Pierce), is added to 10 mg of antibody dissolved in 10 ml of 0.2M sodium bicarbonate pH 8.8 containing 0.15M NaCl. The reaction is allowed to proceed for 15 minutes at room temperature followed by termination of the reaction with 0.1 ml of 1.0M ammonium chloride pH 6.0. The biotinylated antibody is dialyzed against PBS to remove other salts and 1.0 ml aliquots stored at −20° C. To ensure that biological activity of the antibody is maintained following biotinylation, the antibodies are tested by immunoprecipitation of $^{35}S$ methionine labeled cellular extracts containing mutant p53 polypeptides. The monoclonal antibody (0.5 mg) which recognizes mutant p53 polypeptide is reacted with decreasing volumes of sample and immunoprecipitated with 0.05 ml of a streptavidin agarose suspension at 0.24 mg/ml.

Iodination of Purified Antibody For Use in the Antigen-Capture Procedure. Aliquots of 20 $\mu$l of Iodo-Gen (Pierce), which had previously been dissolved in chloroform at a concentration of 10 mg/ml, lyophilized, and kept frozen, are warmed to room temperature. The following are added, in order, to the tube containing Iodo-Gen; 0.025 ml of Buffer II (0.4 Tris-HCl, 0.4 mM EDTA, pH 7.4), monoclonal antibody at a concentration of 1.0 mg/0.1 ml, and 1.0 mCi of $Na^{125}I$ (Amersham # IMS.40). The iodination reaction is allowed to proceed for one minute with gentle shaking and the mixture is subjected to gel filtration chromatography using a G-25 Sephadex™ PD10 column (Pharmacia) equilibrated with 10 mM Tris-HCl, 10 mM NaCl, pH 7.8, to remove unreacted free $^{125}I$. One-half ml fractions are collected and 10% trichloroacetic acid (TCA) precipitable counts determined before the samples are pooled.

Figures 4A, 4B, 4C:
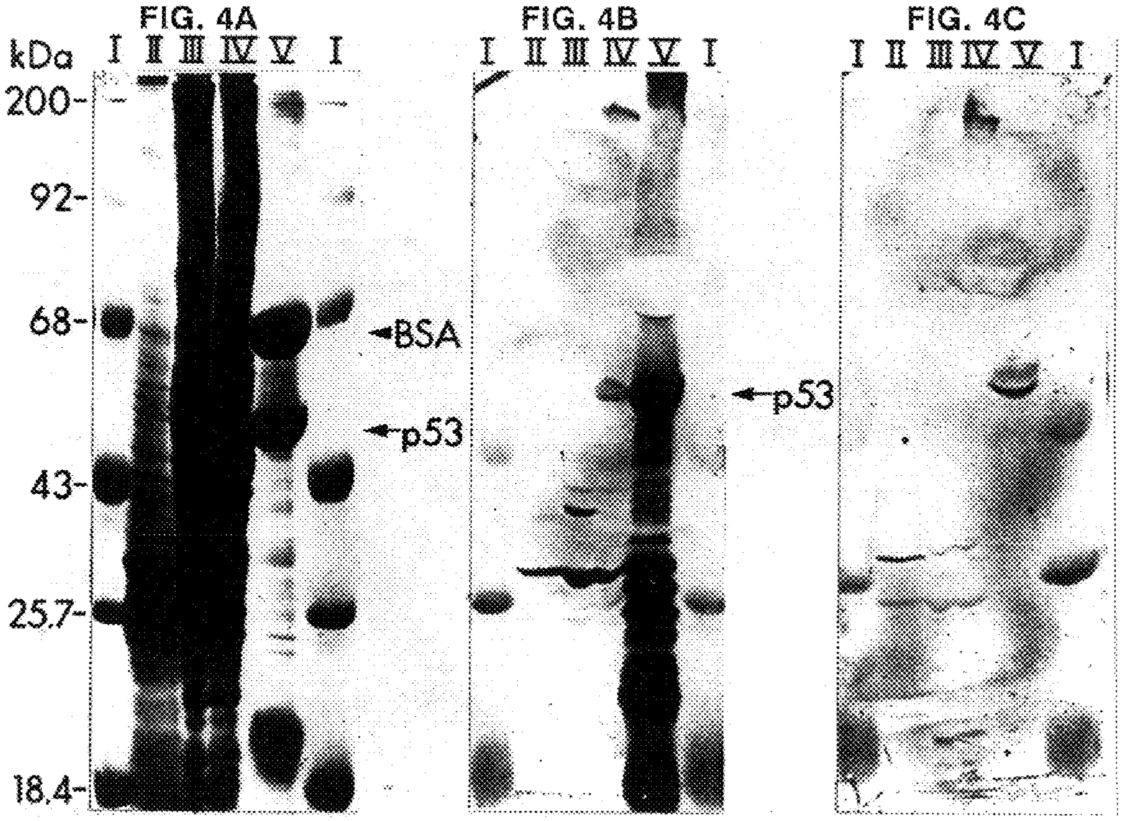
FIGS. 4A–4C Photographs of three gels. Mammalian cell extracts (lanes II–IV, 1 mg protein/lane), purified p53 (lanes V, 5 $\mu$gs/lane) and molecular weight standards (lanes I) were resolved by electrophoresis on a 10% acrylamide gel. The gel was cut into three identical sections and either stained with Coomassie Brilliant Blue G-250 (A) or blotted onto nitrocellulose and incubated with either polyclonal rabbit anti-mutant p53 (HIS175) antibodies (B) or a control rabbit polyclonal antibody of irrelevant specificity (C). Lanes II, K-NRK cell lysates; Lanes III, HL60 cell lysates; Lanes IV, A431 cell lysates.

SDS Polyacrylamide Slab Gol Electrophoresis. Samples are diluted in 20 microliters of sample buffer containing 6.0M urea (Ultrapure, BRL), 0.1M Tris-HCl (Sigma; T-1503), pH 6.8, 15% glycerol (Kodak; 114-9939) 2% sodium dodecyl sulfate (Bio-Rad); #161-07-10), and electrophoresed on a 5 to 20% acrylamide gradient essentially as described by Laemmli (35). The samples are boiled for 2 minutes prior to application to 1–1.5 mm wide slab gel in a Bio-Rad Model 155 Vertical Electrophoresis Cell (Bio-Rad 165-1420) under constant voltage at 45 volts per gel for 15 hours (Hoeffer power supply; PS 1200 DC). Molecular weight standards used are myosin, 200,000; beta-galactosidase, 130,000; phosphorylase B, 92,000; bovine serum albumin, 68,000; ovalbumin, 45,000; carbonic anhydrase, 29,000; soybean trypsin inhibitor, 21,000; lysozyme, 14,400; and cytochrome C, 12,000. Gels are stained with 0.1% Coomassie Blue R-250 (Bio-Rad #16-0400) in 7.0% acetic acid and 10% methanol for five minutes and destained in the same solution without Coomassie (FIG. 4). Certain gels are stained by a silver technique as described by Merril (36) (Bio-Rad silver staining kit; ™1161-0443). Gels containing radioactively labeled samples are subjected to autoradiography as described by Bonner and Laskey (37) using Enhance (New England Nuclear) and type XR-2 X-ray film (Kodak). Molecular weight standards used with gels containing labeled samples are pre-labeled with $^{14}C$ (New England Nuclear).

Quantitation of mutant p53 polypeptide in a biological fluid sample. Quantitation is achieved by the construction of a standard curve using known concentrations of purified, recombinant human mutant p53. By comparing the absorbance obtained from a sample containing an unknown amount of mutant p53 with that obtained from the standards, the concentration of mutant p53 in the sample can be determined (FIGS. 1 and 2).

EXAMPLE 1

Two site sandwich ELISA assay. In a first example, purified monoclonal antibody from clone PAb1801 (5 $\mu$g/ml in 0.1M sodium carbonate buffer, pH 9.0, 100 $\mu$l/well), which binds to both wild-type and mutant p53 polypeptide, is adsorbed onto microtiter wells for 16 to 20 hours at 4° C. The antibody solution is removed from the wells and any remaining protein-binding sites are blocked by incubating the wells with PBS containing 1% BSA at pH 7.2 for 2 hours at room temperature (approximately 23° C.). After blocking, the wells are washed 4-times with 200 $\mu$l of Wash Buffer (PBS containing 0.1% BSA and 0.05% Tween-20, pH 7.3) then appropriately marked wells are incubated with varying amounts of p53 polypeptide-β-galactosidase fusion protein (standard), or the biological sample to be assayed, for 16–18 hours at 4° C. (alternatively for 3 hours at 37° C.). The plates are emptied by inverting over paper towels and the well washed 4-times as described above.

Biotin-conjugated monoclonal antibody from clone PAb421 (reporter antibody) is dissolved in Sample Diluent (PBS containing 50 mM NaCl, 1% normal mouse serum, 0.1% BSA, 0.5% Tween-20and 0.02% Thimerosal) at a concentration of 10 $\mu$g/ml and incubated (100 $\mu$l/well) for 2–3 hours at 37° C. The reporter antibody is bound, in turn, by incubation (1 hour at room temperature) with streptavidin conjugated to horseradish peroxidase (0.4 $\mu$g/ml in Sample Diluent). Wells are washed 4-times, as described above, and a peroxidase substrate solution (e.g. ABTS, 100 $\mu$l/well) is added. After a suitable period of incubation (approximately 60–100 minutes at room temperature) the absorbance is measured at 405 nm.

Sera from 6 normal- and 6 cancer-patient donors was analyzed for mutant p53 polypeptide using the protocol described above.

The average absorbance ($A_{405}$) from duplicate wells for each sample was entered into the regression equation of the standard curve in order to calculate the amount of mutant p53 polypeptide in each of the samples. The maximum sensitivity of the assay is 100 pg/ml. Therefore, samples having no detectable mutant p53 polypeptide are indicated as having less than (<) 100 pg/ml.

Table 2 provides a list of the p53 polypeptide concentrations in sera from 6 normal and 6 cancer patients:

TABLE 2

| Patient | Diagnosis | p53 polypeptide Concentration (pg/ml) |
|---|---|---|
| 1 | Normal | <100 |
| 2 | Normal | 200 |
| 3 | Normal | 200 |
| 4 | Normal | <100 |
| 5 | Normal | <100 |
| 6 | Normal | 1,450 |
| 7 | Breast Cancer | 300 |
| 8 | Colon Cancer | 100 |
| 9 | Stomach Cancer | 1,300 |
| 10 | Colon Cancer | 2,900 |
| 11 | Colon Cancer | 100 |
| 12 | Breast Cancer | 200 |

As described above, the selection of antibodies used in this first example do not distinguish between mutant and wild-type p53 polypeptides and therefore yield a measure of the total (wild-type and mutant) p53 polypeptide concentration in the sample. However, as discussed earlier, wild-type p53 polypeptide does not accumulate to detectable levels; therefore, by inference, the polypeptides detected and measured in these samples are mutant p53 polypeptides. It should also be noted that the mutant p53 polypeptide content of the sample may be influenced by the medical condition of the sample donor, i.e. the patient's tumor burden. This burden is affected by the state of progression of the underlying disease as well as any ameliorative therapy such as surgery, chemotherapy or radiation which may have been administered prior to serum sample collection.

In a second example purified PAb240 is adsorbed onto microtiter wells, since this antibody is specific for the mutant p53 polypeptide. The antibody (5 μg/ml in 0.1M sodium carbonate buffer, pH 9.0; 100 μl/well) is allowed to adsorb for 16 to 20 h at 4° C. The antibody solution is then removed from the wells and any unoccupied protein binding sites are blocked by incubating the wells with PBS containing 1% BSA at pH 7.2 for two hours at room temperature. After blocking, the wells are washed 4-times with 200 μl of Wash Buffer (PBS containing 0.1% BSA and 0.05% Tween-20, pH 7.3) then appropriately marked wells are incubated with varying amounts of purified recombinant mutant p53 polypeptide (standard), or the biological sample to be assayed, for 16–18 h at 4° C. or alternatively for 3 h at 37° C. The plates are emptied by inverting over paper towels, and the wells are washed 4-times as described above.

Polyclonal antibody from rabbits, which recognizes and binds to mutant p53 polypeptide, is dissolved in Sample Diluent (PBS containing 50 mM NaCl, 1% normal mouse serum, 0.1% BSA, 0.5% Tween-20and 0.02% Thimerosal) at a concentration of 5 μg/ml and incubated (100 μl/well) for 2–3 h at 37° C. Bound reporter antibody is, in turn, detected by incubation (1–2 hours at room temperature) with peroxidase conjugated goat anti-rabbit immunoglobulin. After washing the wells, a peroxidase substrate such as ABTS (2,2'-azinodi-[3-ethyl-benzthiazoline sulfonate]) is added, and after a suitable period of incubation (approximately 30–60 minutes at room temperature) the absorbance is read at 405 nm.

Sera from 21 healthy donors and from 67 cancer patients were analyzed for mutant p53 polypeptides using the mutant-specific protocol described above. FIG. 1 shows the standard curve obtained using precise concentrations of purified recombinant human mutant p53 polypeptide. The curve is linear from 0 to 8 ng/ml (linear regression coefficient=0.999).

Figure 5:
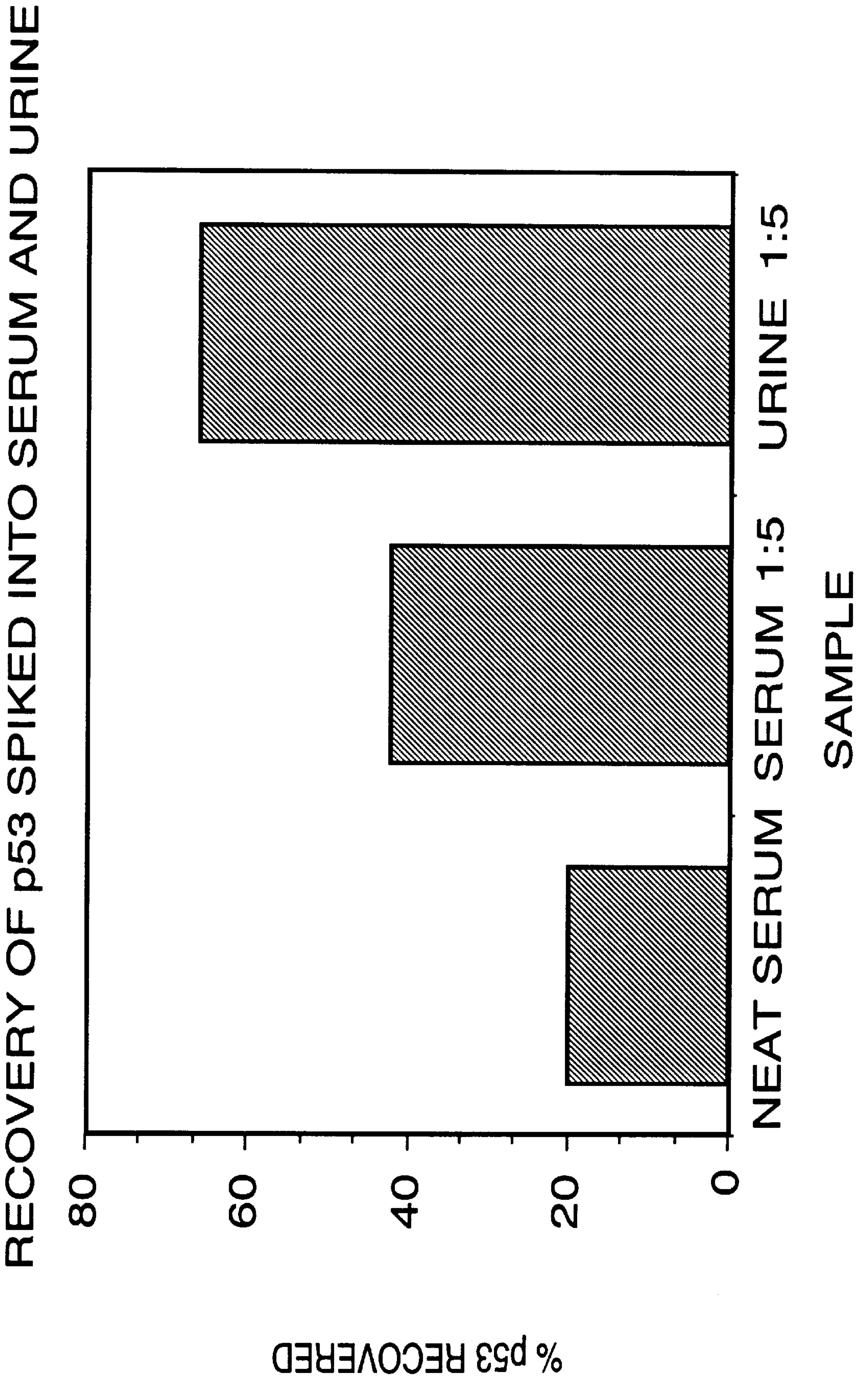
FIG. 5 A bar graph showing recovery of p53 spiked into serum and urine. Purified recombinant mutant p53 was added to undiluted normal serum and to diluted (1:5 with Sample Diluent) normal human serum to a final concentration of 4 ng/ml. Purified p53 was added to diluted human urine to a final concentration of 2 ng/ml. The p53-spiked samples were analyzed in the p53 ELISA assay. The amount of mutant p53 detected is expressed as a percent of the amount actually added to the sample.

Spike and recovery of p53 in normal serum indicated that recovery was better when the serum was diluted (FIG. 5). For example, purified recombinant mutant p53 was added to undiluted normal human serum and to diluted (1:5 with sample diluent) normal human serum to a final concentration of 4 ng/ml. Purified p53 was added to diluted human urine to a final concentration of 2 ng/ml. The p53-spiked samples were analyzed in the p53 ELISA assay. The amount of mutant p53 detected is expressed as a percent of the amount actually added to the sample.

Serum samples were diluted 1:5 with sample diluent and 100 μl of diluted serum was added to duplicate wells for each of the 21 normal and 67 cancer patient samples.

The average absorbance ($A_{405}$) from the duplicate wells for each sample was entered into the regression equation of the standard curve in order to calculate the amount of mutant p53 polypeptide in each of the diluted samples. This amount was then multiplied by the dilution factor (i.e., 5) in order to obtain the amount of mutant p53 polypeptide present in the original, undiluted sera. The amount of mutant p53 polypeptide in the samples is expressed in picograms (pg) per milliliter (ml) of undiluted serum. The maximum sensitivity of the assay is 30 pg/ml. That is, samples having less than 30 pg/ml of mutant p53 polypeptide cannot be detected in this assay and cannot be resolved from each other or indeed from samples having no mutant p53 polypeptide. Since the samples were diluted 1:5, this sensitivity limit becomes 150 pg/ml (30×5). Therefore, in reporting the results of this study, sera samples having no detectable mutant p53 polypeptides are indicated as having less than (<) 150 pg/ml.

Table 3 provides a list of the measured mutant p53 polypeptide concentration from the sera of 21 normal human donors.

TABLE 3

Mutant p53 Polypeptide Concentrations in Normal Human Sera

| Sample | mutant p53 polypeptide Concentration (pg/ml) |
|---|---|
| 1 | <150 |
| 2 | <150 |
| 3 | <150 |
| 4 | <150 |
| 5 | <150 |
| 6 | <150 |
| 7 | <150 |
| 8 | <150 |
| 9 | <150 |
| 10 | 645 |
| 11 | <150 |
| 12 | <150 |
| 13 | <150 |
| 14 | <150 |
| 15 | <150 |
| 16 | <150 |
| 17 | 515 |
| 18 | <150 |
| 19 | 390 |
| 20 | <150 |
| 21 | <150 |

Eighteen of the 21 samples (86%) had no detectable mutant p53 polypeptide (i.e. <150 pg/ml). The three remaining samples (14%) all had mutant p53 polypeptide concentrations which were very close to the limit of assay sensitivity, and no sample had mutant p53 polypeptide in excess of 1000 pg/ml.

Table 4 provides a list of the measured mutant p53 polypeptide concentration from the sera of 67 cancer patients. The cancers were of diverse types, as indicated in Table 4.

TABLE 4

Mutant p53 Concentrations in Cancer Patient

| Sample | Cancer | mutant p53 polypeptide Concentration (pg/ml) |
|---|---|---|
| 14-22-11 | Breast | <150 |
| 89-79-93 | Colon | 417 |
| 91-56-38 | Colon | 444 |
| 5740 | Breast | 218 |
| 5745 | Hodgkins | <150 |
| 5761 | Thyroid | 194 |
| 5755 | Prostate | <150 |
| 5753 | Breast | <150 |
| 5754 | Melanoma | 167 |
| 86 | Colon | 167 |
| 92 | Colon | 306 |
| 85-21-76 | Colon | 194 |
| 16-48-19 | Colon | 194 |
| 92-23-92 | Colon | <150 |
| 127 | Lung | 361 |
| 5387 | lung | 194 |
| 5407 | Lung | 2,472 |
| 5395 | Lung | <150 |

TABLE 4-continued

Mutant p53 Concentrations in Cancer Patient

| Sample | Cancer | mutant p53 polypeptide Concentration (pg/ml) |
|---|---|---|
| 5405 | Colon | <150 |
| 5476 | Breast | <150 |
| 81 | Lung | 361 |
| 18-13-34 | Breast | 333 |
| 54-99-38 | Breast | <150 |
| 5301-18 #30 | Lung | 278 |
| 5301-21 #76 | Lung | 7,261 |
| 5258 | CML | <150 |
| 5257 | CML | 194 |
| 5301-6 #77 | Colon | 167 |
| 5301-8 #85 | Colon | 222 |
| 5255 | CML | <150 |
| 5194 | CML | 194 |
| 5301-2 #9 | Colon | <150 |
| 5301-3 #9 | Colon | 583 |
| 5301-9 #85 | Colon | 167 |
| 5201 | CML | 889 |
| 5200 | CML | 500 |
| 5204 | CML | <150 |
| 5205 | CML | 861 |
| 5206 | CML | 278 |
| 90-77-68 | Stomach | 858 |
| 86-37-76 | Colon | 219 |
| 90-99-19 | Breast | 547 |
| 5764 | Breast | <150 |
| 5301-16 #13 | Breast | 1,168 |
| 5301-19 #37 | Lung | 201 |
| 462 | Colon | 345 |
| 459 | Breast | <150 |
| 461 | Colon | 1,680 |
| 460 | Bladder | 475 |
| 472 | Lung | 1,855 |
| 467 | Breast | 690 |
| 451 | Colon | 2,200 |
| 466 | Kidney | <150 |
| 463 | Kidney | 1,465 |
| 476 | Breast | 1,165 |
| 477 | Bladder | <150 |
| 91-24-57 | Esophagus | <150 |
| 91-27-26 | Larynx | <150 |
| 82-51-90 | Tongue | 1,855 |
| 00-24-40 | Mouth | <150 |
| 33-84-24 | Esophagus | <150 |
| 66-06-89 | Groin | <150 |
| 90-93-82 | Breast | <150 |
| 82-51-54 | Colon | 260 |
| 90-85-81 | Breast | <150 |
| 90-76-03 | Colon | <150 |

In contrast to what was seen in the normal samples, 41 out of the 67 samples tested (61%) had detectable mutant p53 polypeptide; 9 samples (13%) had mutant p53 polypeptide in excess of 1000 pg/ml.

The data presented herewith shows a clear difference in the serum mutant p53 polypeptide concentrations obtained from these two sample populations (i.e. normal versus cancer patient sera). It should be re-emphasized that, for the reasons discussed after the first example, the mutant p53 polypeptide values obtained from the cancer-patient sample probably under estimate the values that would be obtained in otherwise untreated (i.e. newly diagnosed) cancer patients with substantial tumor burdens.

An antibody competition study was conducted in order to verify that the factor being detected in serum from human cancer patients was mutant p53 polypeptide. For this study, two human serum samples were selected. One sample was from a patient with colon cancer (No. 86-37-76). This sample had previously been shown to contain mutant p53 polypeptide when analyzed using the two-site sandwich ELISA (mean value from 8 separate analyses=1.9 ng/ml). The second sample was from a healthy normal donor (OSI #15) that had previously been shown to contain no mutant p53 polypeptide. Each of these two sera were diluted 1:2 with assay buffer, then further divided into two equal portions labeled "experimental" and "control." To each of the experimental tubes was delivered 7.5 μg of purified monoclonal antibody p53 (Ab-2) clone PAb1801 (ATCC Accession No. HB 10642). This is a very well characterized antibody which specifically binds to p53 polypeptide, but does not itself constitute any component of the two-site sandwich ELISA. Each of the control tubes received 7.5 μg of purified monoclonal antibody trpE(Ab-1). This antibody serves as a control since it is of the same isotype ($IgG_1$) as the PAb1801 antibody, but binds specifically to bacterial anthranilate synthetase, a protein which is not present in human serum. However, any IgG1 antibody which is reactive against an irrelevant antigen and which is also not cross-reactive with p53 could serve as a suitable control. For example, two other antibodies which would work equally well as controls are ATTC CRL 1640, an anti-DNA polymerase alpha IgG1 clone or ATTC CRL 1713, an anti-*E. coli* DNA polymerase IgG1 clone.

Figure 6:
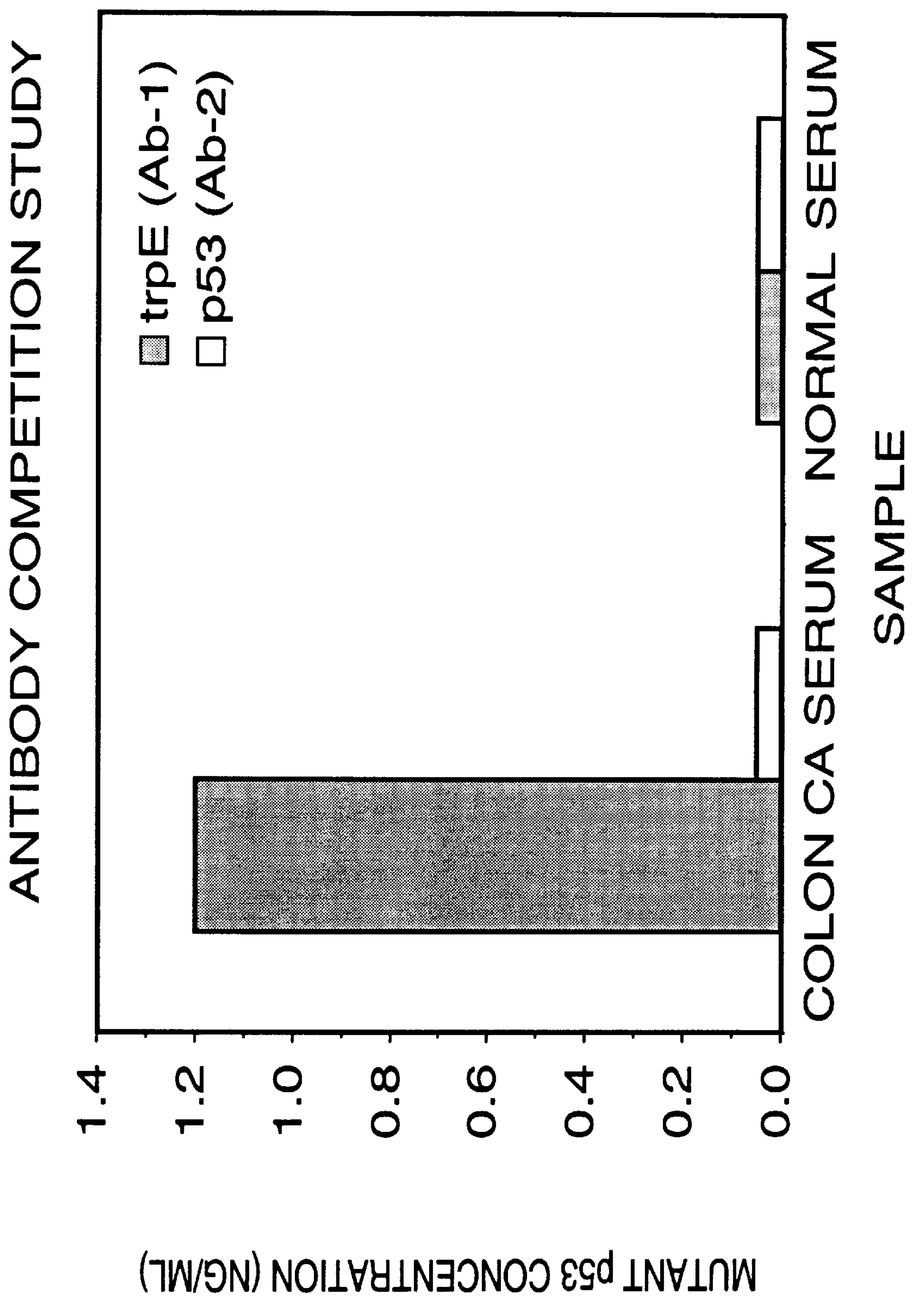
FIG. 6 A bar graph showing that a monoclonal antibody specific for p53 polypeptide (p53 (Ab-2)) will specifically inhibit the reactivity of a mutant p53 containing human cancer serum sample, whereas an antibody to an unrelated protein (trpE(Ab-1)) has no effect. Neither antibody has any effect on a normal serum sample which does not contain any detectable mutant p53 polypeptide. No reactivity is illustrated as a bar having a height equal to 0.05 ng/ml which is the sensitivity limit of this assay.

Each of the samples was then analyzed in the two-site sandwich ELISA. The results show (see FIG. 6) that the addition of the p53 (Ab-2) antibody to the cancer serum sample was sufficient to reduce the signal to undetectable levels whereas the trpE(Ab-1) antibody had no effect. Addition of either antibody to the normal serum sample did not alter finding of no p53 in the normal sample. These results are exactly what would be expected if the factor being detected in the cancer serum sample was p53 polypeptide.

Figure 7:
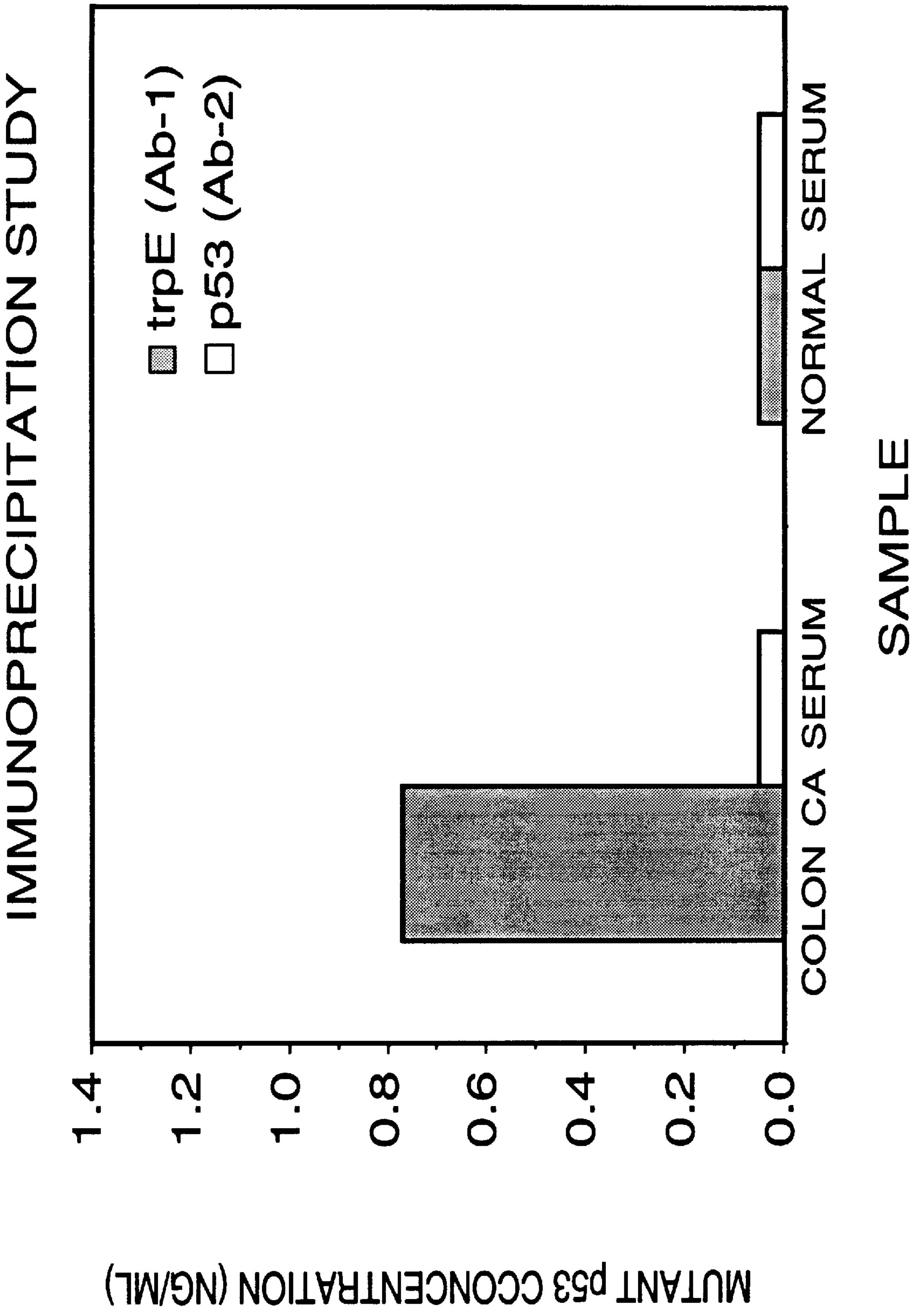
FIG. 7 A bar graph showing that immunoprecipitation with a monoclonal antibody specific for p53 polypeptide (p53 (Ab-2) can be used to efficiently remove any mutant p53 from a serum sample (Colon Ca) containing mutant p53. Under the same conditions, an antibody to an unrelated protein (trpE(Ab-1) does not remove the mutant p53 polypeptide from the sample. Normal serum which does not contain any detectable mutant p53 polypeptide is unaffected by either treatment. No reactivity is illustrated as a bar having a height equal to 0.05 ng/ml which is the sensitivity limit of this assay.

In a further refinement of this study, the experiment was repeated, as described above, except that 35 μl of bacterial Protein A/G (Oncogene Science, Inc., Uniondale, N.Y.) was added to each of the samples. Protein A/G binds to the Fc portion of antibodies. By subjecting the samples to centrifugation (10 min at 4° C., Eppendorf microfuge), the Protein A/G is pelleted along with the bound antibody and any other proteins to which the antibodies have themselves bound. The p53 (Ab-2) clone PAb1801 antibody would thus remove any p53 which may have been present in the sample, whereas the trpE(Ab-1) would leave any p53 in the sample undisturbed. This was done, and the supernatants were analyzed in the two-site sandwich ELISA. The results (see FIG. 7) confirm the above findings.

While the utilization of clone PAb240 as the capture antibody is the preferable configuration, since only mutant p53 polypeptide would be bound, an acceptable alternative would be to have either clone PAb421 or clone PAb1801 serve as the capture antibody. For these alternatives, the assay format would be identical to the one described above. Alternatively, the polyclonal antibody can be used as the capture antibody with PAb240 as reporter. In this configuration, peroxidase conjugated goat anti-mouse immunoglobulin is substituted for the peroxidase conjugated goat anti-rabbit immunoglobulin in the assay format described above.

EXAMPLE 2

Immunoblotting Analysis. Sera samples or cell extracts to be analyzed are first subjected to SDS-PAGE as described hereinabove on 5–20% acrylamide gradient gels. After electrophoresis, transfer of proteins to nitrocellulose (Schleicher & Schuell, BA 85, 0.45 um) is performed.

Proteins are transferred at 70 volts for 2–3 hours at 4° C. The nitrocellulose is incubated in 0.5% non-fat powdered milk (Carnation) in Phosphate buffered saline pH 7.4 (PBS) containing 0.02% sodium azide for 1 hour at room temperature. The filter is then washed with PBS containing 0.1% Tween 20 (Bio-Rad Lab) and incubated with $^{125}$[I] labeled PAb240 monoclonal antibody ($2.0\times10^6$ CPM/ml) diluted in the same buffer for 1.5 hours at 37° C. The filters are washed three times with PBS-Tween-20, dried and exposed to Kodak XR-2 film at −70° C. using intensifying screens. Alternatively, the filter is incubated with PAb240 monoclonal antibody then washed with PBS and incubated with alkaline phosphate-conjugated goat anti-mouse IgG. The filter is washed with PBS and incubated with a suitable alkaline phosphatase substrate (e.g. 5-bromo-4-chloro-3-indolyl-phosphate) until colored bands develop. Further alternatively, the filter is incubated with polyclonal rabbit anti-p53 antibody, washed with PBS and incubated with alkaline phosphate-conjugated goat anti-rabbit IgG. The filter is washed and developed as described above.

EXAMPLE 3

Immunoprecipitation of mutant p53 polypeptide with Immunoglobulin. One ml of sera is reacted for 15 hours at 4° C. with 1 microgram of monoclonal antibody PAb240 and 50 $\mu$l of a 10% (v/v) suspension of Protein-A agarose (BRL) containing 0.175 mg Protein-A. The immunocomplexes are washed three times in PBS TDS and collected by centrifugation at 1000 RPM for 10 minutes. The immunoprecipitates are resolved by electrophoresis using a 5–20% acrylamide SDS-PAGE. The resolved proteins are electrophoretically transferred (blotted) to nylon, nitrocellulose or other suitable membrane support. Blotted membranes are blocked for 1 h in a solution containing PBS and 1% to 10% BSA or casein in order to block nonspecific protein binding sites. The blocked membranes are incubated with radiolabeled antibodies directed against mutant p53 polypeptides (either monoclonal or polyclonal) then subjected to autoradiography. Alternatively, the antibodies directed against mutant p53 polypeptides may be enzymatically labeled and detection effected through the use of an appropriate substrate solution. For example, a peroxidase-labeled antibody could be incubated with 0.03% 4-chloro-1 Naphthol.

In an alternative immunoprecipitation protocol, PAb240 monoclonal antibody is biotinylated according to a protocol distributed by LKB Laboratories. Two hundred microliters of Act BIOTIN solution prepared by adding 2.0 mg of Act BIOTIN to 0.5 ml of anhydrous dimethylformamide (Pierce), is added to 10 mg of PAb240 dissolved in 10 ml of 0.2M sodium bicarbonate pH 8.8 containing 0.15M NaCl. The reaction is allowed to proceed for 15 minutes at room temperature followed by termination of the reaction with 0.1 ml of 1.0M ammonium chloride pH 6.0. The biotinylated antibody is dialyzed against PBS to remove other salts and 1.0 ml aliquots stored at −20° C. To ensure that biological activity of the antibody is maintained following biotinylation, the antibodies are tested by immunoprecipitation of purified, recombinant mutant p53 polypeptides. The PAb240 MoAb (0.5 g) is reacted with decreasing volumes of patient sera containing the mutant p53 polypeptide and immunoprecipitated with 0.05 ml of a strepavidinagarose suspension at 0.24 mg/ml resulting in a PAb240-mutant p53 polypeptide-strepavidinagarose complex which is detectable.

EXAMPLE 4

Solid Phase Antigen Capture Procedure Using Biotinylated Monoclonal Antibodies As Reporter. For each assay point, an aliquot of affinity capture matrix comprising a PAb240 Affi-Gel-10™ suspension is added to a tube containing 4 mls of PBS with 4% BSA, blocked for one half to three hours, pelleted by centrifugation at 2,800 RPM, then washed once in PBS. The blocked, washed capture matrix is used to probe the presence of mutant p53 polypeptides in sera from cancer patients. Patient serum is added to each tube containing a pellet of affinity matrix and allowed to react for one to two hours. The matrix is pelleted and washed once in 4.0 mls of PBS containing 0.05% Tween 20. One ml of PBS and biotinylated PAb240 are added to each tube, incubated at 37° C. for 1 hour, pelleted, then washed once in PBS-0.5% Tween 20. An avidin-biotin-horseradish peroxidase complex is prepared by mixing together two drops of solution A (Vectastain, Avidin Biotin complex (ABC) kit, #PK4004, Vector Laboratories) and 2 drops of solution B in 10.0 ml of PBS containing 0.05% Tween 20. After 30 minutes, one ml of ABC solution is added to the matrix pellet, mixed, and incubated at 37° C. for 30 to 60 minutes. Then matrix is pelleted and washed once with 4.0 mls of PBS-0.5% Tween 20. Developing solution is made as follows: Solution I is prepared by adding 0.06 ml of 30% hydrogen peroxide to 100 ml of PBS. Solution II is prepared by adding 60 mg of horseradish peroxidase developer (BioRad) to 20.0 ml of ice-cold methanol. Immediately before use, 5 parts of solution I is mixed with 1 part of solution II and 1.0 ml added to the matrix. The matrix develops a blue color in samples containing the mutant p53 polypeptide.

Solid Phase Antigen Capture Procedure Using lodinated Antibodies as Reporter Antibodies. One ml of PAb240 capture affinity matrix is washed two times with 4.0 ml of PBS TDS and one time with 4.0 ml of PBS containing 0.1% BSA (PBS-BSA). Capture matrices can be used with either cell extracts or human biological fluids and are incubated in round bottom (12×75 mm, Enkay) or conical polypropylene tubes (12×75 mm, Enkay).

The gel matrix pellet is suspended in two times its volume of PBS containing 0.1% sodium azide, and 0.01 ml is transferred to a round bottom tube, (12×75 mm, Enkay) containing a bacterial growth and protease inhibitor solution (BGIPI, 0.05 ml) of final concentrations of 0.005% TPCK (Sigma), 0.01% soybean trypsin inhibitor (Sigma), 0.01% sodium azide, and 0.01% sodium fluoride and 2.75 $\mu$l (0.054 TIU) of a aprotinin (Sigma) (19.8 TIU/ml). One half of ml of patients or normal human sera (NHS) or cell extract is added to each tube and the sample is incubated overnight at 4° C. The gel matrix is washed 2 times with 3.0 ml PBS, and approximately 0.1 ml volume of liquid is retained with the gel matrix pellet. The pellet is rocked for 2 hours at 37° C. with 0.1 ml of $^{125}$I-labeled antibody directed against mutant p53 polypeptides [monoclonal or polyclonal-approximately 60,000 CPM, 1.0 $\mu$Ci $^{125}$I Iodine per 1.0 microgram protein], washed one time with 3.0 ml of PBS TDS, two times with 3.0 ml PBS, and finally counted in a gamma counter.

EXAMPLE 5

Double diffusion in agar. Molten agar is poured onto glass slides or into petri dishes and allowed to harden. Small wells are punched out of the agar a few millimeters apart. 50 $\mu$l of the affinity purified rabbit polyclonal antibody directed against mutant p53 polypeptides is added to one of the punched out wells and 100 $\mu$l patient sera is added to another punched out well located opposite to the antibody-containing well. These samples are allowed to diffuse toward one another in a moist chamber for 18–24 hours. The resultant precipitation lines represent mutant p53 polypeptide complexes which are analyzed visually in indirect light with the aid of a magnifying lens. The antibody and mutant p53 polypeptide diffuse in a radial fashion, creating an arc which approximates a straight line at the leading edges of the diffusing antibody-mutant p53 polypeptide complex.

EXAMPLE 6

Solution Phase Antigen Capture Test. A solution phase mutant p53 polypeptide capture test which represents an alternative embodiment of the invention has been formatted. This test requires 0.1 ml of patient sera, and the other test components consist of strepavidinagarose (Bethesda Research Laboratories, Rockville, Md., Catalog No. 5942SA, Lab No. 52101), biotinylated capture antibody PAb240 and $^{125}$Iodine-labeled PAb1801 as reporter antibody.

The conditions for optimized performances have been determined. Sera sample (0.1 ml), 3 micrograms biotinylated capture antibody and 100,000 cpm of $^{125}$Iodine labeled reporter antibody are combined, incubated one hour at 25° C., and 16 micrograms strepavidin covalently coupled to agarose are added. Following 30 min. of incubation at 25° C. with shaking, the immunocomplexes are collected by centrifugation at 2,800 rpm for 3 min. in a Beckman refrigerated centrifuge (Model TJ-6), supernatant containing unbound reporter antibody is aspirated and 3 ml of PBS 0.1% Triton X-100 is added. The centrifugation, aspiration and wash steps are repeated three times, and the bound $^{125}$Iodine counts are measured in a LKB gamma counter (Model 1274).

EXAMPLE 7

Radioimmunaassay (RIA). Iodination of recombinant mutant p53 polypeptide is performed as described. The radioimmunoassay utilizes $^{125}$I-mutant p53 polypeptide, unlabeled mutant p53 polypeptide, PAb240, goat anti-mouse IgG and Protein A-agarose and is performed as follows. Fifty microliters of $^{125}$I-mutant p53 polypeptide ($2\times10^4$cpm) is diluted in the biological fluid sample or in increasing concentrations of unlabeled mutant p53 polypeptide standard in phosphate buffered saline containing 1% BSA 0.02% $NaN_3$ (PBS-BSA) and incubated with 5 $\mu$g/ml of PAb240 at 4° C. overnight. Fifty microliters of goat anti-mouse IgG is added (1:1000 in PBS) and incubated at room temperature for 1 hour after which Protein A-Agarose (50 $\mu$l of 10% (v/v)) suspension is added and incubated for 30 min at room temperature. The tubes are centrifuged, washed three times in PBS-1% BSA-0.5% Triton X-100 and counted for radioactivity. The amount of mutant p53 polypeptide in the sample is quantitated from the standard curve constructed with purified unlabeled mutant p53 polypeptide.

RESULTS

Figure 8A:
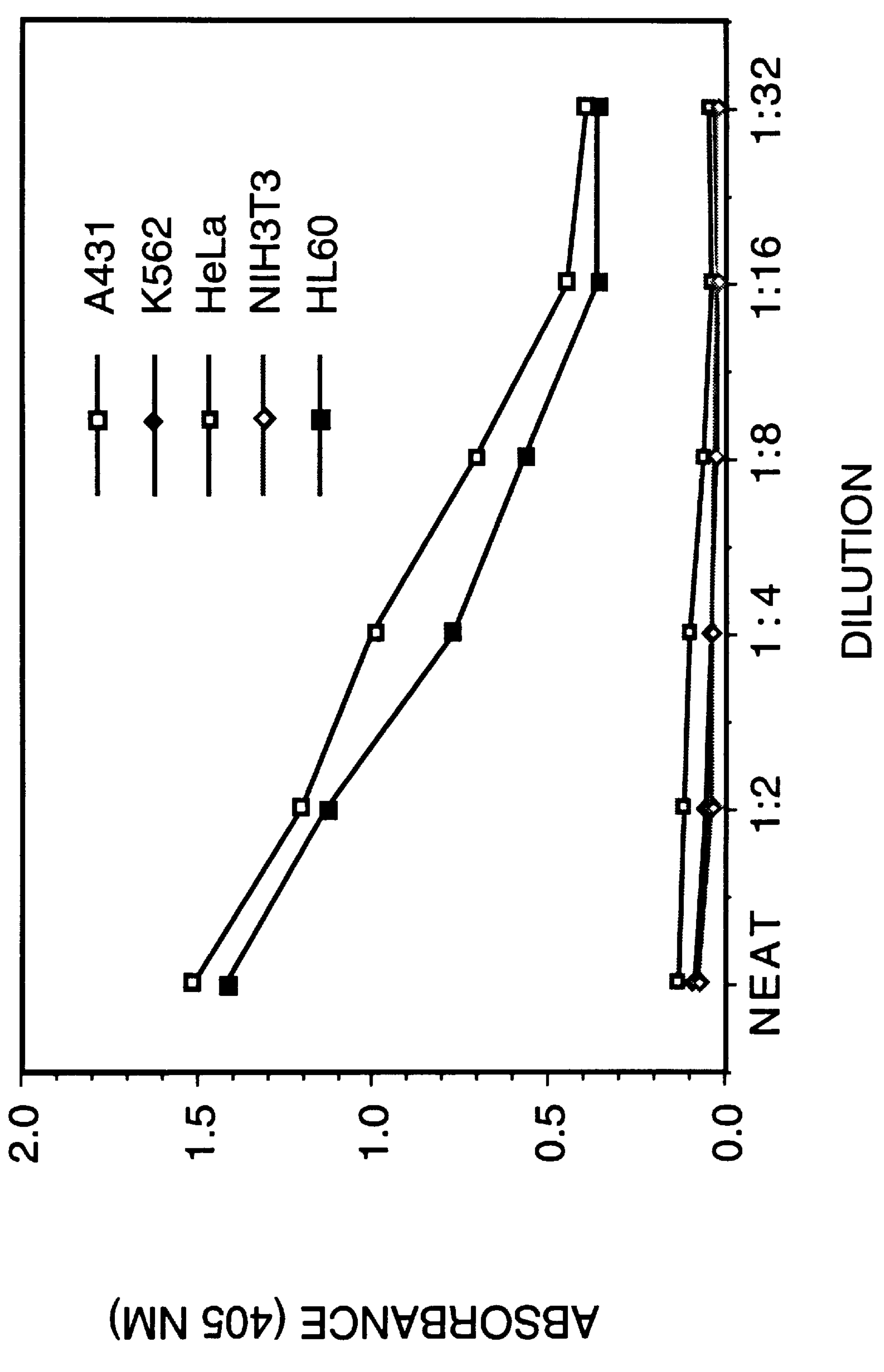
FIG. 8A A line graph showing mutant p53 from diluted mammalian cell lysates. Whole cell extracts were prepared from several mammalian cell lines. Cell extracts were analyzed in the p53 ELISA assay at several different dilutions.
Figure 8B:
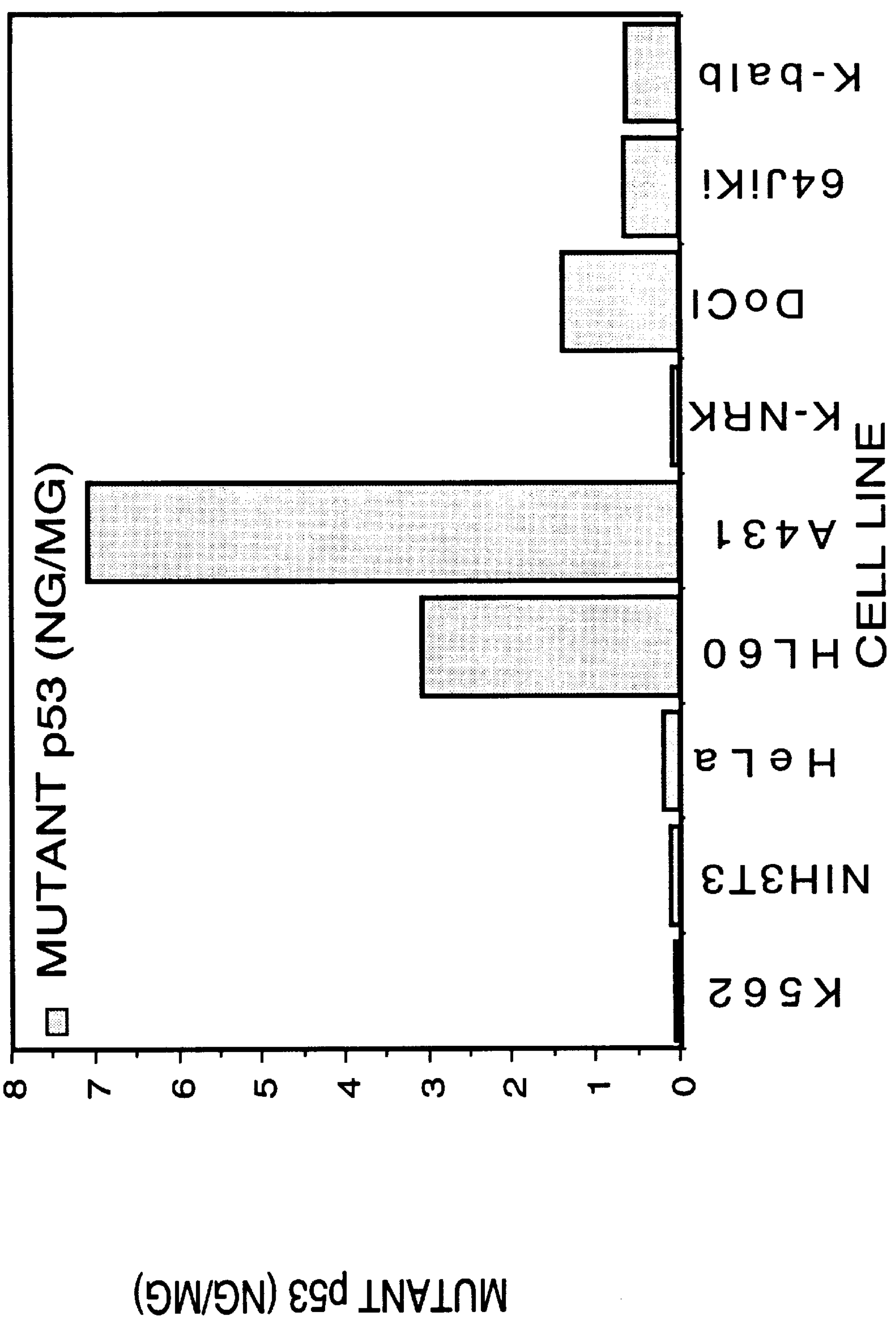
FIG. 8B A bar graph showing mutant p53 in mammalian cell lysates. The amount of mutant p53 in each of the different cell lines was calculated from samples which had been diluted 1:5 with Sample Diluent and expressed relative to the amount of total extracted protein.

A quantitative two-site ELISA for mutant p53 proteins has been developed. The p53 ELISA assay utilizes monoclonal antibody, clone PAb240, to selectively bind those mutant p53 proteins which express the PAb240 epitope. High titer rabbit polyclonal antibodies raised against recombinant mutant p53 (HIS175) are used in the reporter cascade and immunoaffinity purified human recombinant mutant p53 (HIS273) is used as standard in the assay. Sensitivity of 50 pg mutant p53 per/ml of sample buffer is routinely achieved, while better than 20 pg/ml sensitivity can be attained under optimal conditions. Intra- and inter-assay CVs are better than 5% at the mid-range of the standard curve (FIG. 2). No cross-reactivity was found to insulin, transferrin, and a variety of growth factors and interleukins measured at concentrations greater than 2,000 times the sensitivity limits of the assay (Table 5). Nonspecific cross-reactivity was also demonstrated using extracts from mutant p53-negative cell lines as test samples. Little or no mutant p53 was found in whole cell extracts of K562 and KNRK cells (K-ras transformed NRK cells) whereas a high level of expression was found in the human epidermoid carcinoma line A431 (7.1 ng/mg) (FIG. 8). HL60 cells also showed significant levels of mutant p53 (3.1 ng/mg). Expression of mutant p53 in this cell line may differ depending on the particular variant being examined. Low to moderate expression of mutant p53 was detected in virally transformed mouse (k-balb), Mink (64 Jiki) and dog (DoCl) cells. The p53 Assay may be used to measure mutant p53 in human samples from cancer patients.

TABLE 5

Specificity of the p53 ELISA Assay

| Sample Tested | Concentration Tested in The Assay | Assay Results |
|---|---|---|
| bInsulin | 100 ng/ml | <50 pg/ml |
| hTransferin | 100 ng/ml | <50 pg/ml |
| hrIGF-1 | 100 ng/ml | <50 pg/ml |
| hPDGF | 100 ng/ml | <50 pg/ml |
| hG-CSF | 100 ng/ml | <50 pg/ml |
| hrGM-CSF | 100 ng/ml | <50 pg/ml |
| hrIL-1α | 100 ng/ml | <50 pg/ml |
| hrIL-1β | 100 ng/ml | <50 pg/ml |
| hrIL-2 | 100 ng/ml | <50 pg/ml |
| hrIL-3 | 100 ng/ml | <50 pg/ml |
| hrIL-4 | 100 ng/ml | <50 pg/ml |
| hrIL-6 | 100 ng/ml | <50 pg/ml |
| hrTNFα | 100 ng/ml | <50 pg/ml |

The indicated samples were dissolved in Sample Diluent at a concentration of 100 ng/ml and assayed in the p53 ELISA assay. No measurable cross reactivity was observed for any of the tested samples.

REFERENCES

1. Gannon, J. V., et al. (1990) The EMBO J. 9:1595.
2. Lane, D. P., and S. Benchimol (1990) Genes and Develop. 4:1.
3. Bartek, J., et al. (1990) Oncogene 5:893.
4. Iggo, R., et al., (1990) Lancet. 335:675.
5. Sturzbecher, H., et al. (1987) Oncogene 1:201.
6. Sturzbecher, H., et al. (1988) Mol. Cell. Biol. 8:3740.
7. Clarke, C. F., et al. (1988) Mol. Cell. Biol. 8:1206.
8. Finlay, C. A., et al. (1988) Mol. Cell. Biol. 8:531.
9. Eliyahu, D. (1988) oncogene 3:313.
10. Milner, J. and A. Cook (1986) Virology 154:21.
11. Yewdell, J. W. et al. (1986) J. Virol. 59:444.
12. Wolf, D. et al. (1984) Mol. Cell. Biol. 4:552.
13. Wolf, D., et al. (1984) Proc. Natl. Acad. Sci. 82:790.
14. Ben-David, Y. et al. (1988) Oncogene 3:179.
15. Mercer, W. E., et al. (1984) Mol. Cell. Biol. 4:276.
16. Finlay, C. A., et al. (1989) Cell 57:1083.
17. Crawford, L. V., et al. (1984) Mol. Biol. Med. 2:261.
18. Cattoretti, G., et al. (1988) Int. J. Cancer 41:178.
19. Van Den Berg, F. M. et al. (1989) J. Pathol. 157:193.
20. Koeffler, H. P., et al. (1986) Proc. Natl. Acad. Sci. 83:4035.
21. Smith, L. J. et al. (1986) J. Exp. Med. 164:751.
22. Mackay, J., et al. (1988) Lancet II:1384.
23. Baker, S. J. et al. (1989) Science 244:217.
24. James, C. D. et al. (1989) Proc. Natl. Acad. Sci. 86:2858.
25. Yokota, J., et al. (1987) Proc. Natl. Acad. Sci. 84:9252.
26. Nigro, J. M., et al. (1989) Nature 342:705.

27. Hinds, P., (1989) J. Virol. 63:739.
28. Crawford, L. V. et al. (1982) Int. J. Cancer 30:403.
29. Lubbert, M., et al. (1988) J. Exp. Med. 167:873.
30. Harlow, E. et al. (1985) J. Virol. 37:1601
31. Maniatis, T., et al. (1982) Molecular Cloning. A Laboratory Manual. Cold Spring Harbor Laboratory Press, Cold Spring Harbor, N.Y.
32. Sanger, F. et al. (1977) Proc. Natl. Acad. Sci. 74:5463.
33. Ruther, U. and B. Muller-Hill (1983) EMBO J. 2:1791.
34. Kohler, G. (1980) Hybridoma Techniques, Cold Spring Harbor Laboratory Press. Cold Spring Harbor, N.Y.
35. Laemmli, U. K. (1970) Nature 117:680.
36. Merril, C. R., et al. (1981) Science 211:1437.
37. Bonner, W. M. and R. A. Laskey (1974) Eur. J. Biochem. 46:83.

What is claimed is:

1. A method for determining in a subject whether the subject likely has a neoplastic condition which comprises:

(a) obtaining from the subject a sample of serum; and (b) quantitatively determining the concentration of mutant p53 polypeptide present in the sample, the presence of the mutant p53 polypeptide present in the sample at a concentration greater than 150 pg/ml indicating that the subject likely has the neoplastic condition.

2. The method of claim 1, wherein in step (b) the quantitatively determining comprises:

(i) contacting the sample from step (a) with an antibody which forms a complex with the mutant p53 polypeptide under conditions permitting the complex to be formed; and (ii) determining the quantity of the complex so formed.

3. The method of claim 2, wherein the antibody forms a complex with the mutant p53 polypeptide but not with wild-type p53.

4. The method of claim 2 or 3, wherein the antibody is a polyclonal antibody.

5. The method of claim 2 or 3, wherein the antibody is a monoclonal antibody.

6. The method of claim 2 or 3, wherein the antibody is attached to a solid support.

7. The method of claim 2 or 3, wherein the quantitative determination of the complex in step (ii) comprises:

a) contacting the sample from step (i) with a second antibody which forms a second complex with the complex formed in step (i) under conditions permitting the second complex to be formed; and b) determining the quantity of the second complex so formed.

8. The method of claim 7, wherein the second antibody is a polyclonal antibody.

9. The method of claim 7, wherein the second antibody is a monoclonal antibody.

10. The method of claim 7, wherein the second antibody is attached to a solid support.

11. The method of claim 7, wherein the second antibody is labeled with a detectable marker.

12. The method of claim 11, wherein the detectable marker is an enzyme, biotin, a fluorophore, a chromophore, a heavy metal, a paramagnetic isotope, or a radioisotope.

13. A method for quantitatively determining the concentration of mutant p53 polypeptide in a serum sample which comprises:

(a) contacting a solid support with an excess of a first antibody which forms a complex with the mutant p53 polypeptide under conditions permitting the antibody to attach to the surface of the solid support;

(b) contacting the resulting solid support to which the first antibody is bound with the serum sample under conditions such that the mutant p53 polypeptide in the serum binds to the antibody and forms a complex therewith;

(c) contacting the complex formed in step (b) with a predetermined amount of a second antibody directed to an epitope on the mutant p53 polypeptide different from the epitope to which the first antibody of step (a) is directed, so as to form a complex which includes the mutant p53 polypeptide, the first antibody, and the second antibody; and (d) quantitatively determining the amount of the complex formed in step (c), thereby determining the concentration of the mutant p53 polypeptide in the serum sample.

14. The method of claim 13, wherein the first or second antibody forms a complex with the mutant p53 polypeptide but not with wild type p53.

15. The method of claim 13 or 14, wherein the first antibody bound to the solid support is a monoclonal antibody and the second antibody is a polyclonal antibody.

16. The method of claim 13 or 14, wherein the first antibody bound to the solid support is a polyclonal antibody and the second antibody is a monoclonal antibody.

17. The method of claim 13 or 14, wherein the first antibody bound to the solid support is a monoclonal antibody and the second antibody is a monoclonal antibody.

18. The method of claim 13 or 14, wherein the first antibody bound to the solid support is a polyclonal antibody and the second antibody is a polyclonal antibody.

19. The method of claim 13 or 14, wherein the first antibody is labeled with a detectable marker.

20. The method of claim 13 or 14, wherein the second antibody is labeled with a detectable marker.

21. The method of claim 19, wherein the detectable marker is an enzyme, biotin, a fluorophore, a chromophore, a heavy metal, a paramagnetic isotope, or a radioisotope.

22. The method of claim 20, wherein the detectable marker is an enzyme, biotin, a fluorophore, a chromophore, a heavy metal, a paramagnetic isotope, or a radioisotope.

23. A method for monitoring the course of a neoplastic condition in a subject which comprises quantitatively determining in a first sample of serum from the subject the concentration of mutant p53 polypeptide according to the method of claim 13 or 14, and comparing the concentration so determined with the concentration in a subsequent sample from the subject, such samples being taken at different points in time, a difference in the concentrations determined being indicative of the course of the neoplastic condition.

24. The method of claim 13, wherein the amount determined in step (d) is an amount that is equal to or greater than two standard deviations above the concentration of p53 found in samples from normal subjects.

25. The method of claim 13, wherein the first antibody is an antibody which specifically recognizes and binds to an epitope specifically recognized and bound by the antibody produced by hybridoma PAb 1801 deposited at the American Type Culture Collection as ATCC Accession No.: HB10642.

26. The method of claim 13, wherein the first antibody is an antibody which specifically recognizes and binds to an epitope specifically recognized and bound by the antibody produced by hybridoma PAb 240 deposited at the American Type Culture Collection as ATCC Accession No.: HB10614.

27. The method of claim 7 or 13, wherein the second antibody is an antibody which specifically recognizes and binds to an epitope specifically recognized and bound by the antibody produced by hybridoma PAb 1801 deposited at the American Type Culture Collection as ATCC Accession No.: HB10642.

28. The method of claim 13, wherein the first antibody is an antibody which specifically recognizes and binds to an epitope specifically recognized and bound by the antibody produced by hybridoma PAb 240 deposited at the American Type Culture Collection as ATCC Accession No.: HB10614 and the second antibody is an antibody which specifically recognizes and binds to an epitope specifically recognized and bound by the antibody produced by hybridoma PAb 1801 deposited at the American Type Culture Collection as ATCC Accession No.: HB10642.

29. The method of claim 2, wherein the antibody is an antibody which specifically recognizes and binds to an epitope specifically recognized and bound by the antibody produced by hybridoma PAb 1801 deposited at the American Type Culture Collection as ATCC Accession No.: HB10642 or an antibody which specifically recognizes and binds to an epitope specifically recognized and bound by the antibody produced by hybridoma PAb 240 deposited at the American Type Culture Collection as ATCC Accession No.: HB10614.

30. A method for diagnosing in a subject a neoplastic condition which comprises:

(a) obtaining from the subject a sample of a biological fluid, and (b) quantitatively determining the concentration of a mutant p53 polypeptide present in the sample, the presence of the mutant p53 polypeptide in the sample at a concentration equal to or greater than two standard deviations above the concentration of the p53 polypeptide found in samples from normal subjects indicating that the subject has the neoplastic condition, wherein the biological fluid comprises amniotic fluid, blood, serum, plasma, urine, sputum, cerebrospinal fluid, saliva lung lavage, ascites fluid or a mucous-type bodily secretion.

31. The method of claim 30, wherein in step (b) the quantitatively determining comprises:

(i) contacting the sample from step (a) with a protein which forms a complex with the mutant p53 polypeptide under conditions permitting the complex to formed; and (ii) determining the quantity of the complex so formed.

32. The method of claim 31, wherein the protein is an antibody.

33. The method of claim 32, wherein the antibody is a polyclonal antibody.

34. The method of claim 32, wherein the antibody is a monoclonal antibody.

35. The method of claim 31, wherein the protein is a heat shock protein.

36. The method of claim 35, wherein the heat shock protein is selected from the group consisting of HSC 70, HSC 71, HSC 72, HSP 70, and HSP 72.

37. The method of claim 31, wherein the protein specifically forms a complex with type p53 polypeptide but not with a wild type p53 polypeptide.

38. The method of claim 31, wherein the protein is attached to a solid support.

39. The method of claim 31, wherein the quantitative determination of the complex in step (ii) comprises:

(a) contacting the sample from step (i) with a second protein which forms a second complex with the complex formed in step (i) under conditions permitting the second complex to be formed; and (b) determining the quantity of the second complex so formed.

40. The method of claim 39, wherein the second protein is a heat shock protein.

41. The method of claim 40, wherein the heat shock protein is selected from the group consisting of HSC 70, HSC 71, HSC 72, HSP 70, HSP 71, and HSP 72.

42. The method of claim 39, wherein the second protein is an antibody.

43. The method of claim 42, wherein the antibody is a monoclonal antibody.

44. The method of claim 42, wherein the antibody is a polyclonal antibody.

45. The method of claim 42, wherein the second protein specifically forms a complex with the mutant p53 polypeptide but not with a wild-type p53 polypeptide.

46. The method of claim 39, wherein the second protein is a attached to a solid support.

47. The method of claim 31, wherein the protein is labeled with a detectable marker.

48. The method of claim 39, wherein the second protein is labeled with a detectable marker.

49. The method of claim 47 or 48, wherein the detectable marker is an enzyme, biotin, a fluorophore, a chromophore, a heavy metal, a paramagnetic isotope, or a radioisotope.

50. The method for monitoring the course of neoplastic condition in a subject which comprises quantitatively determining in a first sample of a biological fluid from the subject the concentration of a mutant p53 polypeptide and comparing the concentration so determined with the concentration in one or more subsequent samples from the subjects said first sample and said subsequent samples being taken at different points in time, wherein the biological fluid comprises amniotic fluid, blood, serum, plasma, urine, sputum, cerebrospinal fluid, saliva, lung lavage, ascites fluid or a mucous-type bodily secretion, the presence of the mutant p53 polypeptide in the first sample or in the one or more subsequent samples at a concentration equal to or greater than two standard deviations above the concentration of the p53 polypeptide found in samples from normal subjects indicates that the subject has the neoplastic condition at the point in time the corresponding sample was taken, and a difference in the concentrations determined being indicative of the course of the neoplastic condition.

* * * * *